(12) United States Patent
Hursh

(10) Patent No.: US 6,579,233 B2
(45) Date of Patent: Jun. 17, 2003

(54) SYSTEM AND METHOD FOR EVALUATING TASK EFFECTIVENESS BASED ON SLEEP PATTERN

(75) Inventor: Steven Rawlings Hursh, Joppa, MD (US)

(73) Assignee: Science Applications International Corp., San Diego, CA (US)

( * ) Notice: Subject to any disclaimer, the term of this patent is extended or adjusted under 35 U.S.C. 154(b) by 0 days.

(21) Appl. No.: 09/899,540

(22) Filed: Jul. 6, 2001

(65) Prior Publication Data

US 2003/0013943 A1 Jan. 16, 2003

(51) Int. Cl.[7] .................................................. A61B 5/00
(52) U.S. Cl. ...................... 600/300; 600/544; 128/920
(58) Field of Search ............................. 600/300–301, 600/509, 515, 521, 544–545, 595; 128/898, 920–925; 607/88, 2.4, 25, 27, 19; 514/288

(56) References Cited

U.S. PATENT DOCUMENTS

| | | | |
|---|---|---|---|
| 4,893,291 A | | 1/1990 | Bick et al. |
| 5,006,985 A | | 4/1991 | Ehret et al. |
| 5,111,391 A | | 5/1992 | Fields et al. |
| 5,140,562 A | | 8/1992 | Moore-Ede et al. |
| 5,176,133 A | * | 1/1993 | Czeisler et al. ............. 600/509 |
| 5,270,920 A | | 12/1993 | Pearse et al. |
| 5,303,170 A | | 4/1994 | Valko |
| 5,323,314 A | | 6/1994 | Baber et al. |
| 5,615,138 A | | 3/1997 | Tanaka et al. |
| 5,682,882 A | * | 11/1997 | Lieberman .................. 600/300 |
| 5,845,257 A | | 12/1998 | Fu et al. |
| 5,970,466 A | | 10/1999 | Detjen et al. |
| 5,970,468 A | | 10/1999 | Bull |
| 6,070,098 A | * | 5/2000 | Moore-Ede et al. ........ 600/544 |
| 6,135,117 A | * | 10/2000 | Campbell et al. ........... 128/898 |
| 6,313,749 B1 | * | 11/2001 | Horne et al. ................. 340/575 |
| 6,419,629 B1 | * | 7/2002 | Balkin et al. ............... 600/300 |

OTHER PUBLICATIONS

P. Achermann, et al., "Combining Different Models of Sleep Regulation", Journal of Sleep Research, 1991, pp. 144–147, 1.

T. Akerstedt, et al., "Validation of the S and C Components of the Three–Process Model of Alertness Regulation", Sleep, 1991, pp. 1–6, 19(18).

R. Angus, et al., "Effects of Sleep Loss on Sustained Cognitive Performance During a Command and Control Stimulation", Behavior Research Methods, Instruments, & Computers, 1985, pp. 55–67, 17(1).

G. Belenky, et al., "Sustaining Performance During Continuous Operations: The U.S. Army's Sleep Management System", 1996, Paper Presented At The 1996 Army Science Conference.

(List continued on next page.)

Primary Examiner—Max F. Hindenburg
Assistant Examiner—Michael Astorino
(74) Attorney, Agent, or Firm—Banner & Witcoff, Ltd.

(57) ABSTRACT

A method for evaluating the effectiveness of a person to perform a task based on his/her previous or predicted sleep activity is provided. The method can be used to predict changes in task effectiveness at any time of day, based upon numerous patterns of sleep and activity, either experienced or planned for the future. The method take into account progressive increases in sleep deprivation, the effects of the time of day on performance, and changes in the time when a person sleeps and works. The method also accounts for the quality of a sleep interval and a person's sleep inertia, the temporary slowing of performance immediately after awakening. The method is homeostatic. Gradual decreases in sleep debt decrease sleep intensity. Progressive increases in sleep debt produced by extended periods of less than optimal levels of sleep lead to increased sleep intensity. As a result the method can predict the normal decline in sleep intensity during the sleep period and the normal equilibrium of performance under less than optimal schedules of sleep.

48 Claims, 11 Drawing Sheets

OTHER PUBLICATIONS

B. Bjerner, et al., "Diurnal Variation of Mental Performance. A Study Of Three–Shift Workers", British Journal of Industrial Medicine, 1955, pp. 103–110, 12.

A. Borbely et al., "Concepts and Models of Sleep Regulation: An overview," Journal of Sleep Research, 1992, pp. 63–79, 1.

A. Borbely et al., "Sleep Initiation and Initial Sleep Intensity: Interactions of Homeostatic and Circadian Mechanisms", Journal of Biological Rhythms, 1989, pp. 149–160, 4 (2).

M. Carskadon, et al., "Sleep Tendency: An Objective Measure of Sleep Loss", Sleep Research, 1977, 6, 200.

D. Dinges, et al. "Sleepiness Impairs Optimum Response Capability", Sleep Research, 1989, 18, 366.

S. Folkard, "Diurnal Variation In Logical Reasoning", British Journal of Psychology, 1975, pp. 1–8, 66 (1).

S. Folkard et al., "A Three Process Model Of The Regulation Of Alertness And Sleepiness". Sleep, Arousal and Performance Problems and Promises, 1991, 11, 26.

S. Folkard, et al., "Towards A Model For The Prediction Of Alertness And/Or Fatigue On Different Sleep/Wake Schedules In Contemporary Advances In Shiftwork Research", Medical Academy, 1987, pp. 231–240.

S. Folkard et al., "Shiftwork and Performance", Human Factors, 1979, pp. 483–492, 21.

J. Froberg, "Twenty–Four–Hour Patterns In Human Performance, Subjective And Physiological Variables And Differences Between Morning And Evening Active Subjects", Biological Psychology, 1977, pp. 119–134, 5.

R.C. Graeber, "Recent Studies Relative To The Airlifting Of Military Units Across Time Zones", Chronobiology: Principles and Applications to Shifts in Schedules, 1980, pp. 353–370.

W. Harris, "Fatigue, Circadian Rhythm and Truck Accidents in Vigilance", 1977, pp. 133–147.

P. Hamelin, "Lorry Drivers Times Habits in Work and Their Involvement in Traffic Accidents", Ergonomics, 1987, pp. 1323–1333, 30.

Haus et al., "The Circadian Time Structure", Chronobiology: Principals & Applications to Shifts in Schedules, 1980, pp. 47–94.

S. Hursh, et al., "Modeling Human Performance To Predict Unit Effectiveness", Army Science: The New Frontiers, Military and Civilian Applications, Saratoga, 1993, pp. 309–328.

K. Klein, et al., "Air Operations and Circadian Performance Rhythms", Aviation Space and Environmental Medicine 1976, pp. 221–229, 47(3).

Klein et al., "The Effect of Transmeridian and Transequitorial Air Travel on Psychological Well–Being and Performance", Chronobiology: Principles and Applications to Shifts in Schedules, 1980, pp. 339–352.

J.T. Klopcic, "The Aura Fatigue and Heat Stress Algorithms", (Unclassified): Ballistic Research Laboratory Technical Report BRL–MR–3802, 1989.

R. Kronauer, "A Model for the Effect of Light on the Human "Deep" Circadian Rhythm" Sleep Research, 1982, 16, 620.

P. Lavie, "The 24–hour sleep propensity function (SPF): Practical and theoretical implications", Sleep, Sleepiness and Performance, 1991, pp. 65–93.

P. Lavie, "To Nap Perchance to Sleep—Ultradian Aspects of Napping," Sleep and Alertness: Chronobiological, behavioral, and medical aspects of Napping, 1989, pp. 99–120.

M. Mitler et al., "Multiple Daytime Nap Approaches to Evaluating The Sleepy Patient", Sleep 5, 1982, pp. 119–127.

T. Monk, "Circadian Aspects Of Subjective Sleepiness: A Behavioral Messenger?"Sleep, Sleepiness and Performance, 1991, pp. 39–63.

T. Monk, "Subjective Ratings Of Sleepiness; The Underlying Circadian Mechanisms", Sleep 10, 1987, pp. 343–353.

T. Monk, "The Arousal Model of Time of Day Effects in Human Performance Efficiency", Chronobiologia, 1982, pp. 49–54.

T. Monk et al., "A Field Study of Circadian Rhythms in Actual and Interpolated Task Performance" in Night and Shift Work: Biological and Social Aspects, 1981, pp. 473–480.

J. Ribak et al., "Diurnal Rhythmicity and Airforce Flight Accidents Due to Pilot Error", Aviation, Space and Environmental Medicine, 1983, pp. 1096–1099, 54.

D. Richardson, et al., "Excessive Daytime Sleepiness in Man: Multiple Sleep Latency Measurement in Narcoleptic and Control Subjects", Electroencephalography and Clinical Neurophysiology, 1978, pp. 621–627, 45.

E. Voigt, Int. Z. angew. Physiol. Einschl. Arbetisphysiol., 1968, pp. 1–12, 25.

R. Wever, "Mathematical Models of Circadian One– and Multi–Oscillator Systems", Lect. Math Life Science, 1987, pp. 205–265, 19.

R. Wever, "Use of Light To Treat Jet Lag: Differential Effects of Normal and Bright Artificial Light on Human Circadian Rhythms", Annual NY Academy Science, 1985, pp. 282–304, 453.

R. Wilkinson, "Effects Of Up To 60 Hours Of Sleep Deprivation On Different Types Of Work", Ergonomics, 1964, pp. 175–186, 17.

* cited by examiner

SYSTEM AND METHOD FOR EVALUATING TASK EFFECTIVENESS BASED ON SLEEP PATTERN

BACKGROUND OF THE INVENTION

1. Field of the Invention

The present invention relates to a system and method for evaluating the effectiveness of a person to perform a task based on his/her preceding or predicted sleep pattern. More particularly, the present invention relates to a system and method for evaluating task effectiveness based on preceding or predicted sleep pattern using calculations that take into account circadian oscillators, a sleep reservoir, sleep intensity, performance use, sleep debt, interruptions to sleep, sleep inertia, and the demands of the task to be performed.

2. Background of the Invention

Numerous studies have been conducted relating to the analysis of sleep, alertness, and performance. One study is by Jewett and Kronauer, entitled "Interactive Mathematical Models of Subjective Alertness and Cognitive Throughput in Humans," *J. Biological Rhythms*, 1999; 14(6): pages 588–597. The Jewett and Kronauer model (JK model hereafter) uses arbitrary units and then scales the result from 1 to 0 to fit the actual data, scaled from maximum to minimum. Consequently, the JK model does not make an independent prediction of performance without knowing the range of the results.

The JK model makes no provision for predicting the detrimental effects of sleep fragmentation and multiple interruptions in sleep. The JK model uses an oscillator with a large number of arbitrary parameters (van der Pol oscillator) to predict the asymmetrical cycle of performance around the clock. The JK model cannot adjust the phase of the circadian rhythm to reflect shift-work or transmeridian travel without detailed information about ambient light levels. Furthermore, the JK model cannot predict variations in any relevant aspect of operator performance that is of interest to the user.

U.S. Pat. No. 5,433,223 to Moore-Ede et al. discloses a method for predicting alertness and bio-compatibility of a work schedule of an individual. All of the methods described in Moore-Ede et al. are designed to predict alertness, not performance.

As represented by the foregoing examples, prior studies and patents do not provide a system or method for evaluating the effectiveness of a person to perform a specific task based on his or her previous sleep pattern. In addition, the prior studies are not designed to predict changes in task effectiveness based upon the pattern of sleep and activity that take into account many complex factors that contribute to the sleep experience.

SUMMARY OF THE INVENTION

The forgoing and other deficiencies are addressed by the present invention, which is directed to a system and method for evaluating the effectiveness of a person to perform a task based on his/her previous or predicted sleep pattern. The system and method can be used to predict changes in task effectiveness at any time of day, based upon numerous patterns of sleep and activity (wakefulness), either experienced or planned for the future. The system and method take into account progressive increases in sleep deprivation (fatigue), the effects of the time of day (circadian rhythms) on performance, and changes in the time when a person sleeps and works (shift work and trans-meridian phase shifts).

The system and method for evaluating the effectiveness of a person to perform a task can be employed to schedule sleep and wake periods relative to specific tasks depending on the skills required for the task, such as helping to schedule drivers and pilots to avoid the problems caused by fatigue. Furthermore, the system can be used to anticipate the detrimental effects of jet lag, the beneficial effects of naps, the variations in performance and attention due to circadian rhythms, the variations in sleep quality with time of day and environmental conditions, the safest times to perform difficult tasks, and to help determine when to take sedatives or stimulants, if needed. The system and method may be used to retrospectively analyze the sleep history of a person making a performance error, such as driving a truck off the road, in order to determine if the error was, potentially, related to fatigue and/or circadian variations in performance.

BRIEF DESCRIPTION OF THE DRAWINGS

These and other attributes of the present invention will be described with respect to the following drawings in which.

DETAILED DESCRIPTION OF THE INVENTION

Figure 1:
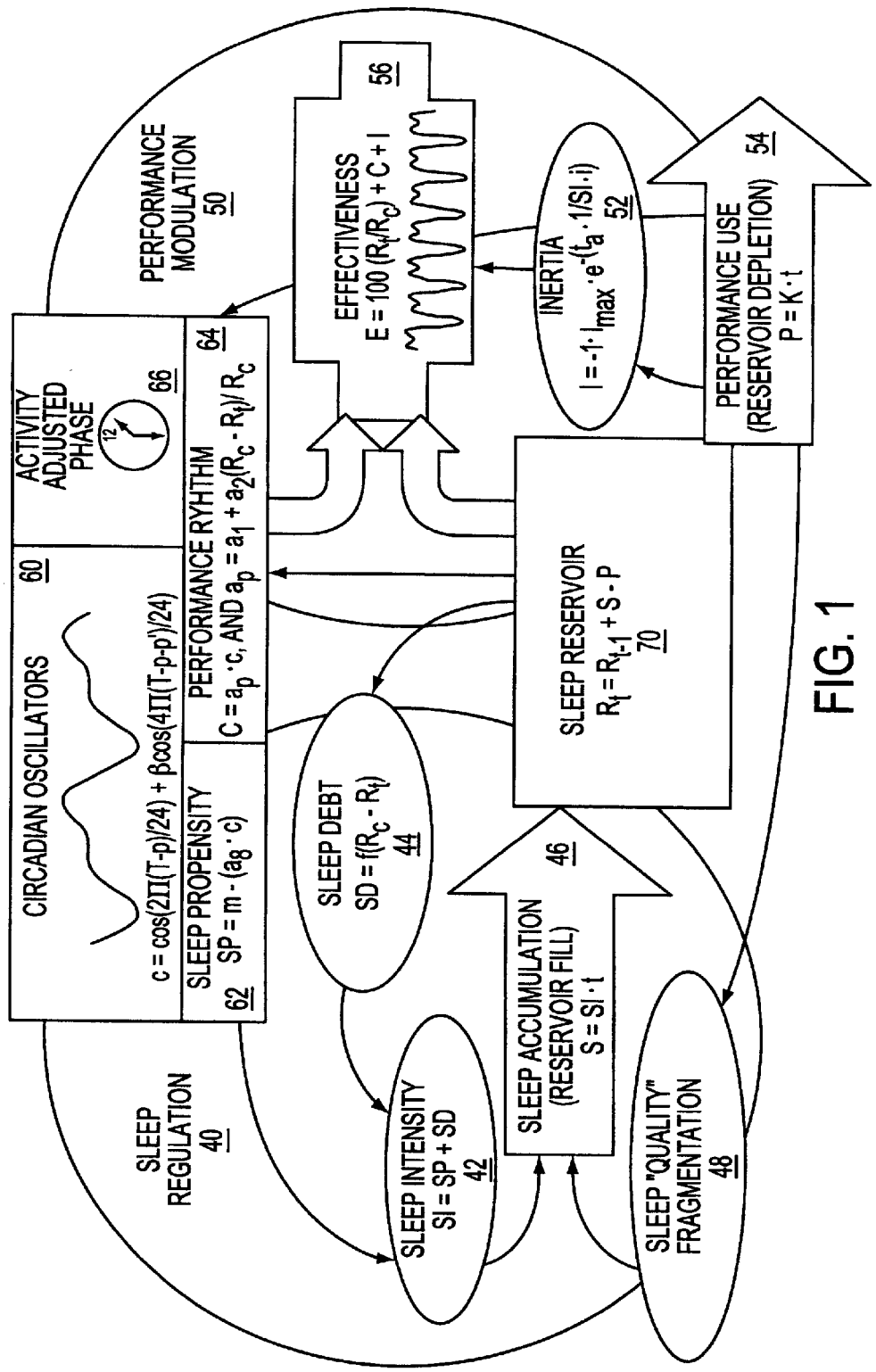
FIG. 1 shows a method and system for evaluating the effectiveness of a person to perform a task according to the present invention.

Referring to FIG. 1, a method and system for evaluating the effectiveness of a person to perform a specific task according to the present invention is illustrated. A user can employ the system to predict modulation of performance based on regulation of a sleep pattern. The factors utilized to regulate sleep are broadly indicated in the sleep regulation section 40, shown in FIG. 1. These factors include sleep intensity 42, sleep debt 44, sleep accumulation 46, and sleep quality or fragmentation 48. Performance modulation section 50 contains factors that are used for such performance modulation, including circadian rhythm 64, sleep inertia 52, effectiveness 56 and performance use 54, as shown in FIG. 1.

A circadian process 60 influences both the performance modulation 50 and sleep regulation 40. Sleep regulation 40 is dependent on the hours of sleep and wakefulness, current sleep debt, the circadian process, which is represented by the circadian oscillators 60, and fragmentation 48, namely awakenings during periods of sleep. Performance modulation 50 depends on the current balance of the sleep reservoir, the circadian process, and sleep inertia. Through the implementation of mathematical modeling the system and method of the present invention can predict changes in cognitive performance. One embodiment of the present invention makes use of a multi-oscillator circadian process, a circadian sleep propensity process, a sleep fragmentation process, and a circadian phase adjusting feature 66 for time zone changes. These processes can be implemented on a general-purpose digital computer.

Performance while awake and the drive to sleep are both controlled, in part, by a circadian process 60. Numerous studies of performance, reaction time, alertness ratings, measures of the tendency to fall asleep, and body temperature indicate that the underlying circadian process is not a simple sine wave. Performance and alertness reach a major peak in the early evening, about 2000 hours, and fall to a minimum about 0400 hours. There is a secondary minimum in the early afternoon, about 1400 hours, and a morning peak at about 1000 hours. Correlated with this pattern is a rising tendency to fall asleep that reaches a peak at about the same time performance and alertness reach a minimum. The existence of both a major and a minor peak in performance and two corresponding minima at other times, suggest that at least two oscillators are involved in the circadian process. These multiple oscillators are accounted for in the method for evaluating the effectiveness of the present invention.

Figure 2:
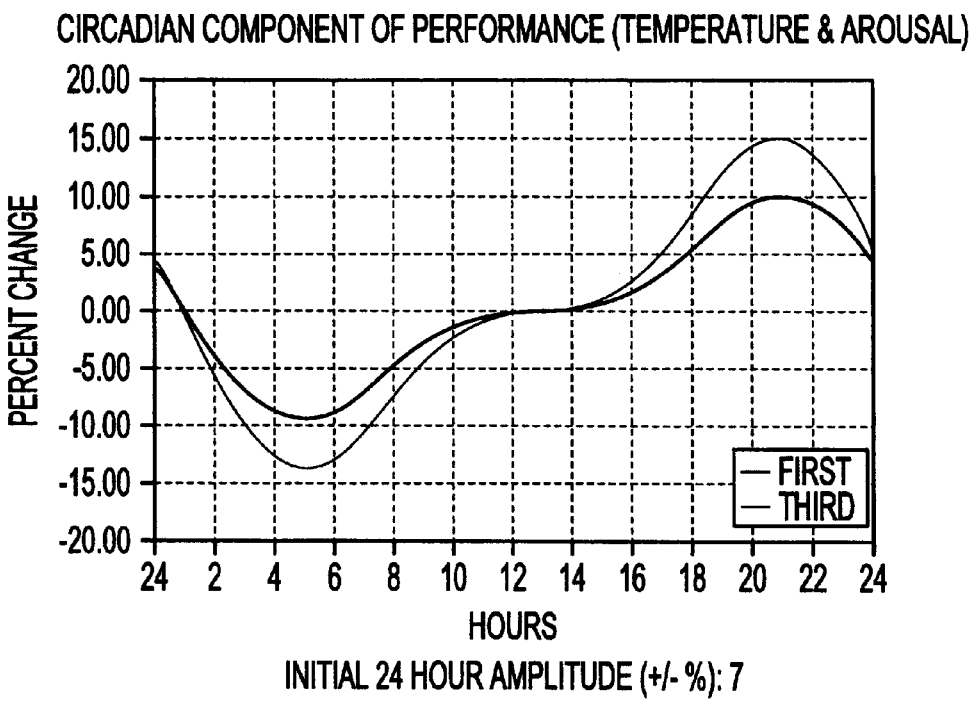
FIG. 2 is a graph illustrating a complex circadian oscillator using units of percent change in effectiveness.

One embodiment of the present invention incorporates a circadian process that is composed of the sum of two cosine waves, one with a period of 24 hours, and one with a period of 12 hours. The two sinusoidal oscillators are out of phase thereby producing a predicted variation in arousal that closely parallels known patterns of body temperature. Referring to FIG. 2, a graph of the complex circadian oscillator is illustrated using units of percent change in effectiveness in one variation of the invention.

The circadian process within the method for evaluating the effectiveness generates an arousal function that mirrors circadian changes in oral temperature. This arousal oscillator drives both variations in predicted cognitive effectiveness and sleep propensity. These two translations of the oscillator have identical frequency and phase components and differ only in amplitude and sign; a rise in arousal produces an increase in performance and a decrease in propensity to sleep. The circadian process 60 is depicted in FIG. 1.

The control of sleep and the influence of sleep on cognitive capacity is a homeostatic process. At the center of the homeostatic process is the sleep reservoir 70, shown in FIG. 1. A fully rested person has optimal performance capacity, indicated as the reservoir capacity $R_c$. While awake, the reservoir is depleted according to a performance use function, indicated by the arrow 54 pointing away from the reservoir 70. While asleep, the reservoir is filled to replenish the capacity to perform and be alert as indicated by the arrow 46 representing sleep accumulation. The rate of accumulation for each minute of sleep is called sleep intensity, and is driven by two factors: 1) the circadian variation in sleep propensity 62, and 2) the current sleep deficit 44, which is the reservoir capacity $R_c$ minus the current level of the reservoir $R_t$ at time t. This deficit is constantly changing as a person sleeps and replenishes the reservoir 70, or is awake and depletes the reservoir 70. The effectiveness 56 is determined from the circadian oscillators 60 and performance rhythm 64, the sleep reservoir 70, and the sleep inertia 52.

The circadian oscillators 60 are represented by the following equation:

$$c = \cos(2\Pi(T-p)/24) + \beta\cos(4\Pi(T-p-p')/24),$$

where

T=time of day, p=24 hr phase in hours, p'=12 hr relative phase in hrs, and β=rel. amplitude of 12 hr cycle.

The sleep propensity is represented by the following equation:

$$SP = m - (a_s \cdot c)$$

where m=mesor (a point around which a sine wave oscillates), and $a_s$=sleep propensity amplitude.

The performance rhythm is represented by the following equation:

$$C = a_p \cdot c$$

where $a_p = a_1 + a_2(R_c - R_t)/R_c$, performance rhythm amplitude.

The connection of the sleep reservoir to the sleep debt calculation 44 forms a feedback loop with the sleep intensity 42, the sleep accumulation 46, and back to the sleep reservoir 70. The sleep debt is represented by the following equation:

$$SD = f(R_c - R_t),$$

where $R_c$=Reservoir Capacity, $R_t$=Current Reservoir Balance, ($R_c - R_t$)=Current Reservoir Deficit, and f=amplitude of feedback.

The reservoir balance of the sleep reservoir 70 is represented by the following function:

$R_t = R_{t-1} + S - P$, and represents the total sleep units at time interval t.

The sleep intensity 42 is represented by the following equation:

$SI = SP + SD$, in sleep units per minute, $SI \leq SI_{max}$

The sleep inertia 52 is represented by the following equation:

$$I = -1 \cdot I_{max} \cdot e^{-(t_a \cdot 1/SI \cdot i)},$$

where max=$I_{max}$, and i=inertia time constant for two hr after awakening.

The sleep accumulation 46 is represented as:

$$S = SI \cdot t,$$

Where t=time interval.

Sleep fragmentation 48 caused by a poor quality sleep environment results in a pause in sleep accumulation after returning to sleep following each awakening from a sleep interval.

The performance use 54 can be represented by the following linear equation:

$$P = K \cdot t,$$

where K=performance use rate.

The prediction of the model is cognitive effectiveness 56 interpreted as percent of baseline cognitive throughput and calculated by the equation:

$$E = 100(R_t/R_c) + C + I$$

Table 1 shows the default values for the variables in the foregoing equations.

TABLE 1

DEFAULT VALUES OF VARIABLES:

| | |
|---|---|
| p = 24 hr component phase in hours | 1700 hrs initially, adjusts to 3 hr after average awake hour according to algorithm described in Attachment B. |
| p' = 12 hr component relative phase in hrs | 3 hrs earlier than p |
| β = relative amplitude of 12 hr cycle | 0.5 |
| m = sleep propensity mesor | 0 |
| $a_s$ = sleep propensity amplitude | 0.55 sleep units |
| $a_1$ = constant performance rhythm amplitude factor | 7 percent |
| $a_2$ = variable performance rhythm amplitude factor | 5 percent |
| $R_c$ = Reservoir Capacity | 2880 sleep units - units required for 4 days continuous awake |
| f = amplitude of feedback | 0.0026243 |
| $SI_{max}$ = maximum sleep unit accumulation per min | 4.4 units per min |
| Sleep fragmentation pause in sleep accumulation | 5 min delay after start of new sleep interval |
| i = inertia time constant for two hr after awakening | 0.04 |
| $I_{max}$ = maximum inertia following awakening | 5 percent |
| K = performance use rate | 0.5 units per minute |
| t = time interval | 1 minute |
| $t_a$ = time awake | Minutes since awakening |

Figure 14:
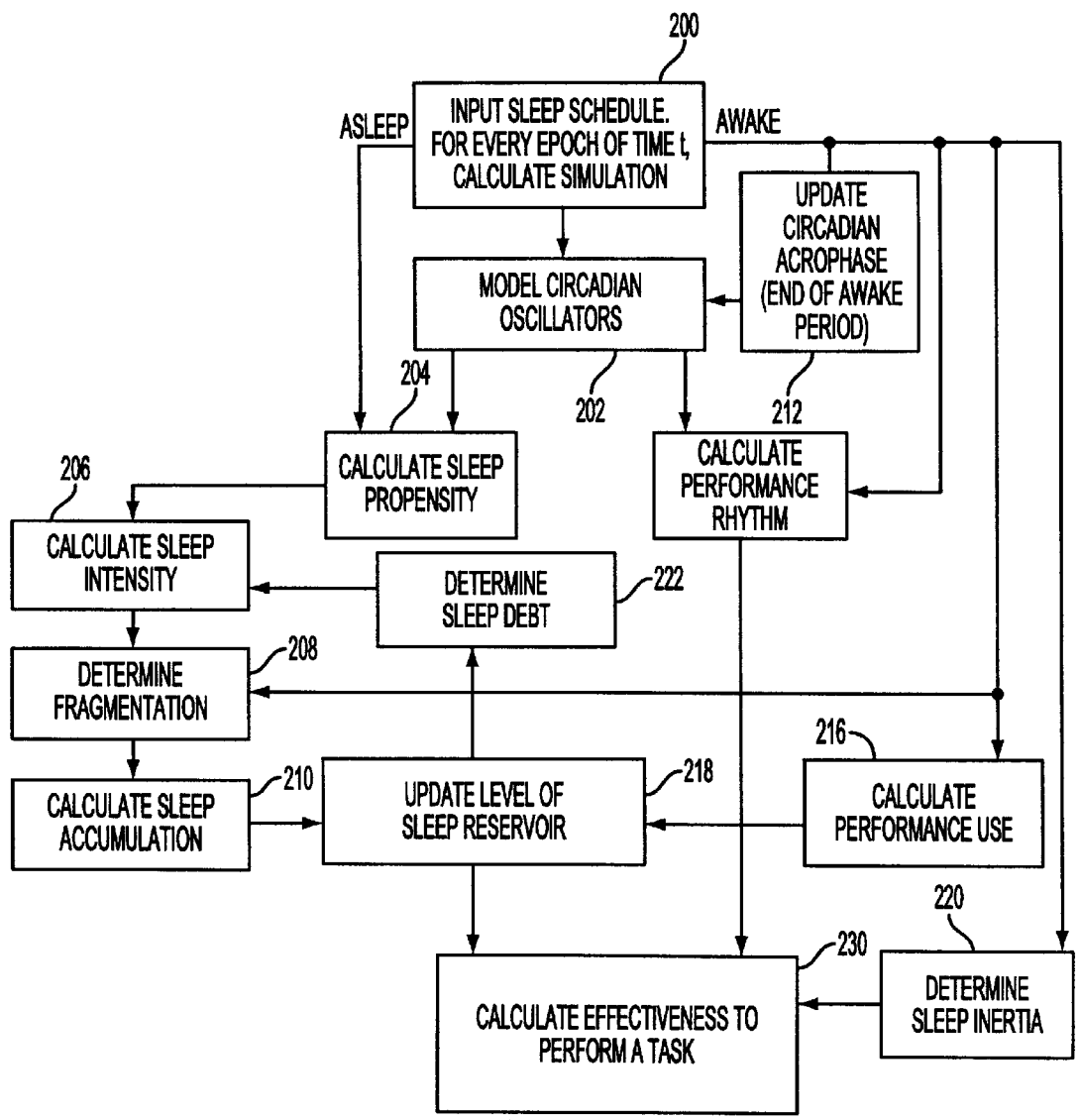
FIG. 14 is a flow chart of a method for evaluating the effectiveness of a person to perform a task according to the present invention.

A method according to the present invention is also illustrated in the flow chart shown in FIG. 14. In step 200 the sleep schedule (past and/or future) is input to the simulation. At each time epoch, t, of the schedule, the sleep state (asleep or awake) is determined and the simulation is updated accordingly. In step 202 the circadian oscillators are modeled. When asleep, the circadian oscillators are used to calculate the sleep propensity 204, which partly determines sleep intensity in step 206. After any pause caused by fragmentation 208, sleep accumulation is calculated in step 210, which is used to update the amount of effective sleep in the sleep reservoir 70 in step 218. The sleep debt is determined in step 222 based on the sleep reservoir calculated in step 218 and is used in step 206 to calculate the sleep intensity. When awake, performance use is calculated in step 216 and also triggers a sleep fragmentation determination in step 208. At the start of each awake period, sleep inertia is calculated in step 220 and contributes to the cognitive effectiveness calculation at 230. The sleep inertia from step 220, the amount of effective sleep in the reservoir 70, calculated in step 218, and the circadian oscillators, modeled in step 202 are used to calculate the performance rhythm at step 214, are all used to calculate the effectiveness to perform the task in step 230. Steps 218, 222, 206, 208 and 210 form a feedback loop.

Figure 3:
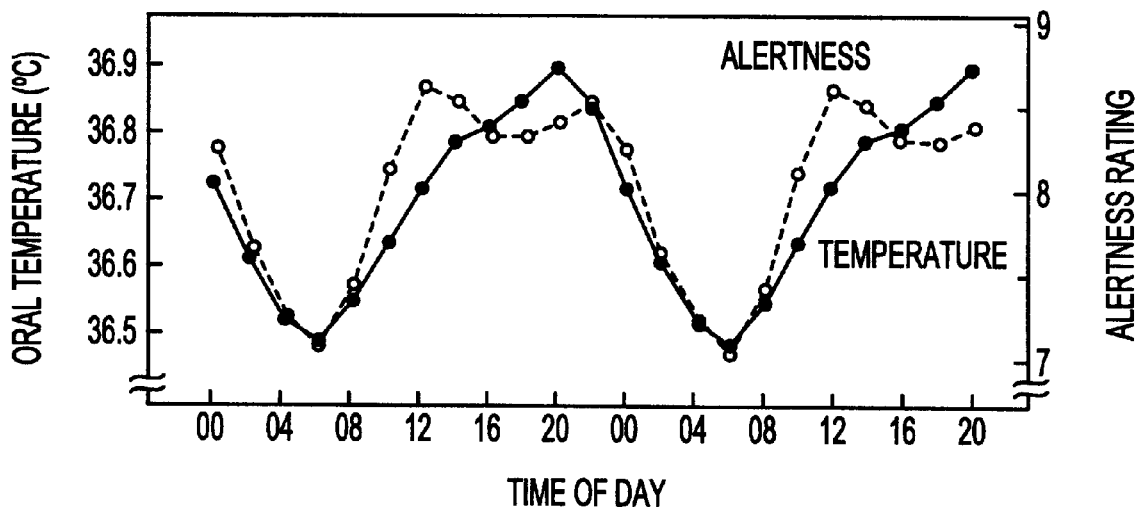
FIG. 3 is a graph illustrating circadian rhythm in oral temperature and substantive alertness.

FIG. 2 is a graph representing circadian oscillation in performance corresponding to the temperature and arousal rhythm as a function of the time of day. The arousal oscillator 60 drives both variations in predicted performance (cognitive effectiveness) and sleep propensity. These two translations of the oscillator have identical frequency and phase components and differ only in amplitude and sign. A rise in arousal produces an increase in performance and a decrease in propensity to sleep. FIG. 2 illustrates an inventive simulation of the performance rhythm for the first day of a fully rested person and after three days of sleep deprivation. The amplitude of the performance rhythm increases with the accumulated sleep debt on the third day. As can be seen in FIG. 3, the circadian rhythm, as represented by oral temperature, and the subjective alertness are closely related, but not identical since alertness and performance are also sensitive to level of the sleep reservoir. The oscillation in the reservoir level is called the sleep-wake cycle and represents the current sleep debt ($R_c-R_t$). Sleep accumulation does not start immediately upon retiring to sleep. Following a period of wakefulness there is a minimal delay of approximately 5 minutes required to achieve a restful sleep state. This factor accounts for the penalty during recuperation that is caused by sleep in an environment that leads to frequent interruptions. These components of the sleep accumulation function are indicated as 42 and 48, respectively, in FIG. 1, to the left of the sleep reservoir 70 feeding into the sleep accumulation function 46.

The level of the reservoir 70 at time t+1 is the level at time t, $R_t$, plus sleep accumulation (S) while asleep and minus performance use (P) while awake. The units of the reservoir 70 are minutes of effective sleep. The method of the present invention can easily accommodate a complex pattern of sleep and waking. While asleep, the simulation adds to the reservoir 70; while awake the simulation depletes the reservoir 70. A schedule can oscillate between these states as often as once a minute and the simulation will keep account of the net effects on performance capacity as the balance in the reservoir 70, similar to the balance in a check book.

The total reservoir capacity is 2880 units (nominal minutes) of effective sleep. This value is based on the following considerations. The average person is assumed to require 8 hours of sleep and is awake for 16 hours in the typical day. To remain in balance, then, sleep units must accumulate at twice the rate it is used during performance.

Hence, the rate of performance use, κ, is 0.5 relative to the average rate of sleep accumulation. Studies of total sleep deprivation indicate that cognitive capacity depletes at a rate of about 25% per day. Hence, the reservoir has the capacity to sustain performance for four days. This translates into 2880 units of sleep: 4 days×24 hours×60 min/hr×0.5.

The outcome of the reservoir process, according to the method of the present invention, during continuous sleep converges to an exponential accumulation function, if one ignores the circadian effects on sleep intensity. One embodiment of the method of the present invention is based on minute-by-minute additions to the reservoir 70 during sleep, with the size of these increments proportional to the reservoir deficit (the feedback process). Integrated over time, this iterative process is described by an approximate exponential function, but is not an exponential function; rather, it is a moment-by-moment simulation of the effects of sleep on the reservoir balance. Therefore, the method can easily accommodate a momentary interruption in sleep (fragmentation) caused by a poor quality sleep environment. The incremental process is interrupted for the duration of the awakening and the reservoir 70 is depleted for that period of time by the performance function. Upon return to sleep after an interruption, there is a delay before resumption of sleep accumulation, with the delay set at 5 min in one embodiment of the method. The result of this process is directly tied to real world events that drive the process, not to an a priori mathematical equation.

The feedback process of the method of the present invention is used to determine the effects of long schedules of less than optimal sleep. Such schedules deplete the reservoir 70, and increase the intensity of sleep when sleep occurs. Eventually, the greater average intensity of sleep permits the person to adjust to such a schedule and find a new equilibrium of sleep and stable performance, within limits. Performance will not be as effective as it might be with a full eight hours of sleep, but performance does not necessarily degrade indefinitely. This is what is meant by a homeostatic sleep and performance process. It is much like a person adjusting to a restricted diet; the person loses weight and conserves energy so that a new equilibrium stable weight is reached under the limited input of calories.

According to the method of the present invention, cognitive effectiveness and alertness are primarily dependent on variations in the two processes just described: the endogenous circadian rhythm (reflected in oral temperature) and current sleep reservoir balance resulting from the sleep-wake cycle. A third factor is a temporary disturbance in performance that may occur immediately following awakening, called sleep inertia I.

The variations in measured alertness, shown in FIG. 3 as a dashed line, do not exactly match the variations in oral temperature. This is because, according to one aspect of the present invention, simulated cognitive effectiveness is computed as the sum of these three factors: the relative level of the sleep reservoir in percent units ($100 \times Rt/Rc$) plus the effects of the circadian oscillator, C, and minus sleep inertia, I. Sleep inertia is represented as an exponential decay function of sleep intensity at the time of awakening and lasts for at most 2 hours.

The predictions are normally in terms of changes in cognitive effectiveness, expressed as percent of baseline performance for a person when well rested. This measure corresponds to performance of a standard serial add-subtract task or the average of a range of standard cognitive tests, described below in greater detail. In addition, the parameters of the performance calculation can be adjusted to predict other components of performance, such as reaction time, lapses in attention, and target error.

The method of the present invention can be used to make a number of predictions, such as for example, performance and alertness. The average person is assumed to require eight hours of sleep per day to be fully effective and to avoid accumulation of sleep debt. Based on the joint interaction of the endogenous circadian oscillator, c, and the sleep-wake cycle, performance is predicted to have two peaks in percent effectiveness at approximately 1000 hours and 2000 hours, a minor dip in performance at about 1400 hours, and a major trough in effectiveness during the early morning hours when the person is normally asleep.

Figure 4:
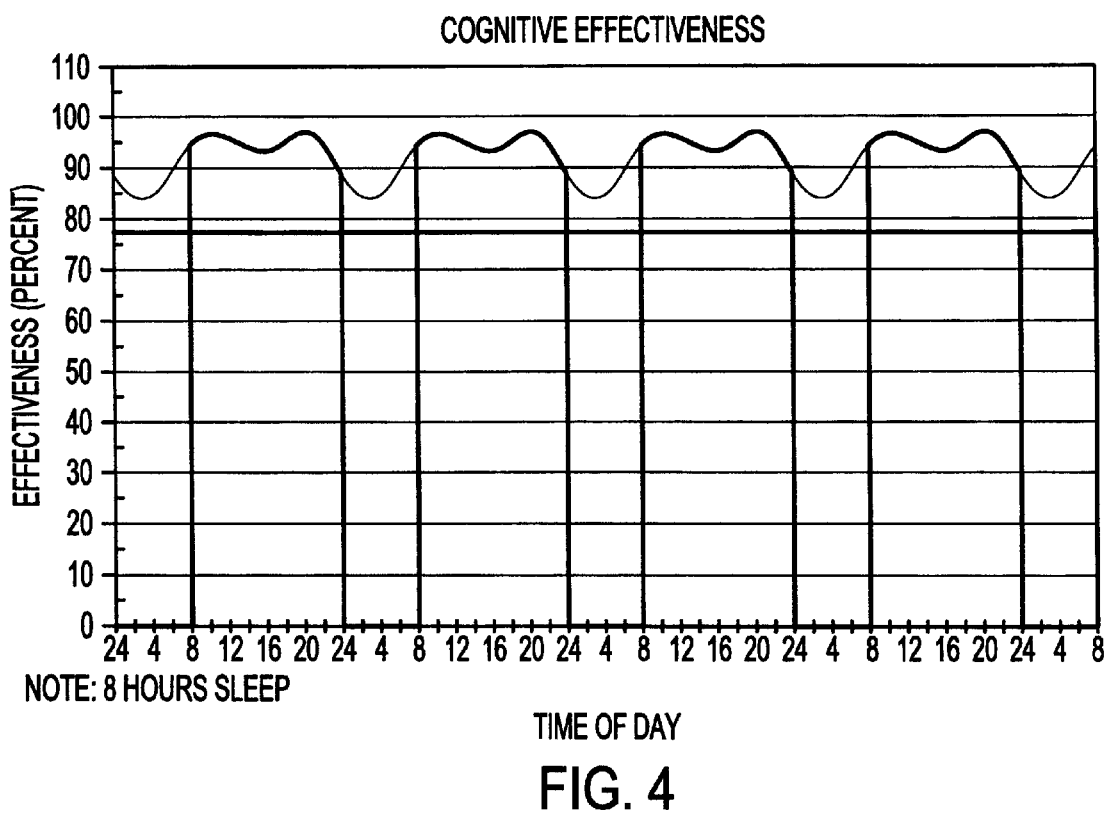
FIG. 4 is a graph illustrating the predicted variations in performance for a person sleeping eight hours per day from midnight to 0800 hours according to one variation of the present invention.

FIG. 4 displays the predicted variations in performance for a person sleeping eight hours per day from midnight to 0800 hours, heavy line. Since the individual is asleep between midnight and 0800, predicted performance is shown as a fine line indicating potential effectiveness, if awake. The nighttime pattern reveals a major trough in performance at about 0300 hours and a minor trough in performance at about 1400 hours. Referring to FIG. 3, the empirical pattern of alertness closely parallels the prediction of the method of the present invention with two peaks in alertness, a mid-afternoon dip in alertness, and a major trough in alertness at 0600 hours. Note that what is important is the pattern of performance and alertness, not the exact time of peaks and troughs, which is a parameter of the model.

Figure 5:
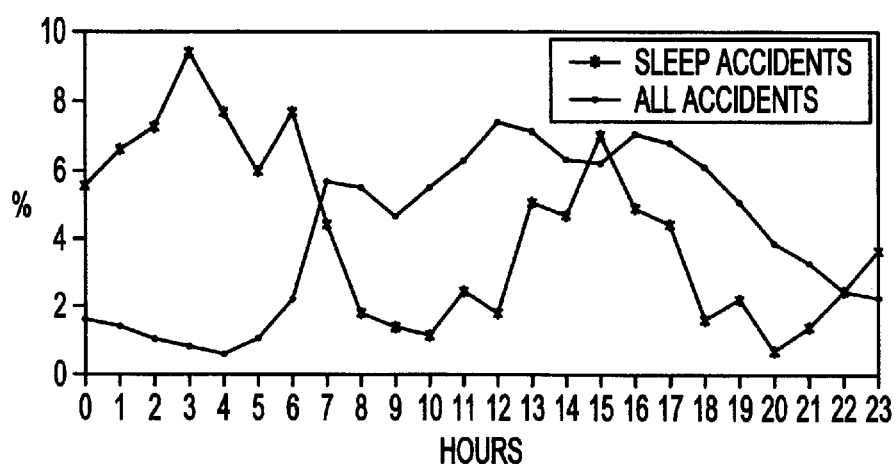
FIG. 5 is a graph illustrating hourly distribution of traffic accidents in Israel caused by falling asleep while driving, for six years, 1984–1989, in comparison with all traffic accidents.

A number of studies agree with the bimodal pattern of performance shown in FIGS. 3 and 4. Lavie (1991) reported the results of a study of sleep related traffic accidents in Israel between 1984 and 1989. In FIG. 5, the connected stars reveal two peaks in sleep related accidents, a major peak at about 0300 hours and a minor peak at about 1500 hours in the afternoon. These correspond to the dips in performance predicted by the model in FIG. 4.

Figure 6:
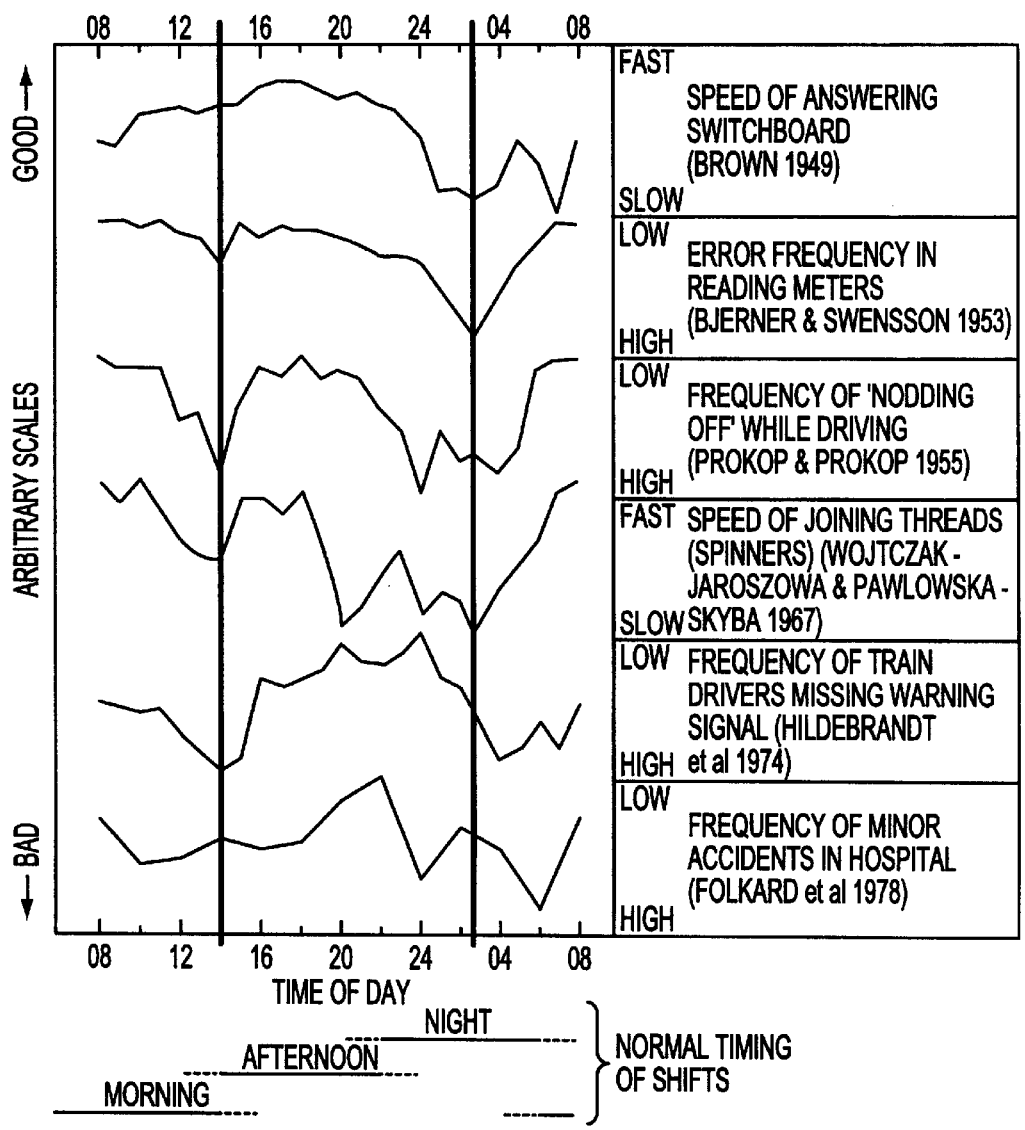
FIG. 6 is graph illustrating circadian rhythm of various industrial activities.

FIG. 6 shows the results from a variety of studies of performance from industrial settings. All performances are scaled so that "good" performance was high on the y-axis and "bad" performance was low on the y-axis. Generally, there were two dips in performance, one at about 0300 hours and a second at about 1400 hours. All these results are consistent with the predictions of the model shown in FIG. 4.

Figure 7:
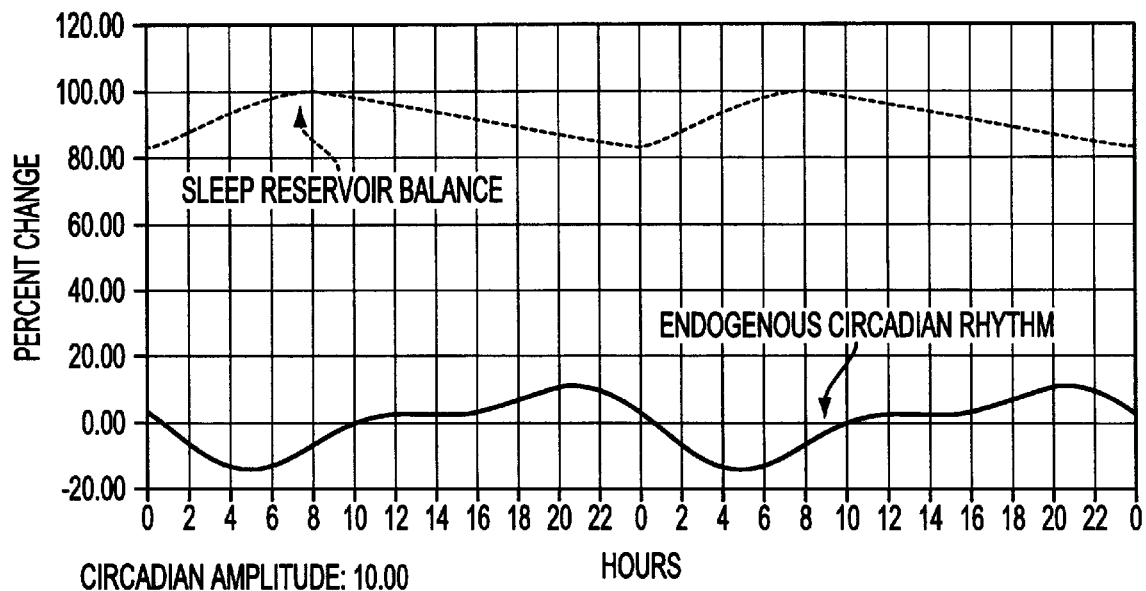
FIG. 7 is a graph illustrating constituents of performance rhythm—sleep reservoir balance and endogenous circadian rhythm of temperature and arousal according to one variation of the present invention.

The basis for the performance pattern shown in FIG. 4 is illustrated in FIG. 7. Within the model, performance is the sum of two major factors, the oscillation of the sleep reservoir balance, top curve, and the oscillation of the circadian arousal process, bottom curve. The two curves are roughly in phase so that as sleep debt is accumulated while awake (top curve), the circadian arousal process is increasing and largely offsets the change in performance. Performance is not perfectly constant, however, for two reasons. First, the two processes are not exactly in phase and this causes a strong early morning trough when the two cycles are both decreasing. Second, the temperature rhythm displays an afternoon plateau and is responsible for the mid-afternoon dip in performance when sleep debt accumulates while temperature is roughly constant.

Figure 8:
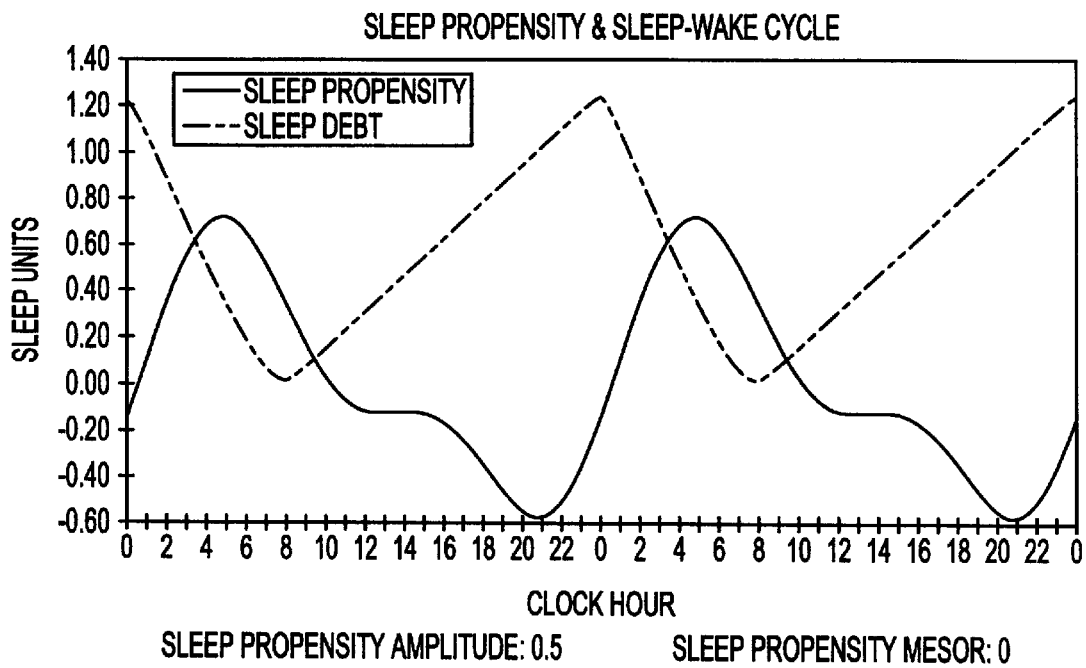
FIG. 8 is a graph showing circadian sleep propensity and sleep debt, according to one variation of the present invention.

As described earlier, the circadian process produces an oscillation in sleep propensity, shown as the solid line in FIG. 8. This rhythm is the negative of the arousal rhythm shown in FIG. 2 and scaled in sleep units. Sleep propensity SP combines with the current sleep debt SD resulting from the sleep-wake cycle, shown as the dashed line in FIG. 8.

Figure 9:
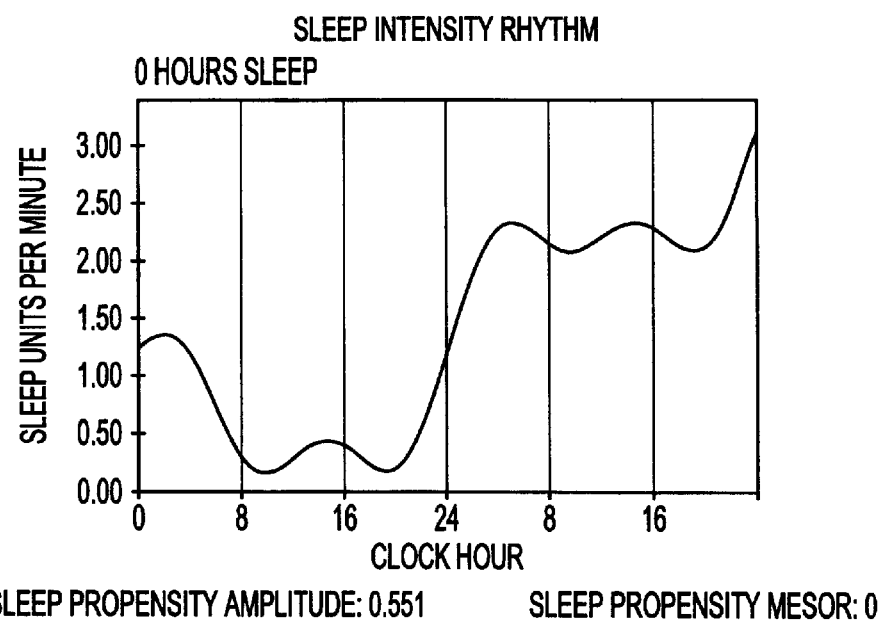
FIG. 9 is a graph illustrating sleep intensity, according to one variation of the present invention.

The summation of this sleep-wake cycle and the circadian process is called sleep intensity SI and is diagrammed in FIG. 9. For a person taking a normal 8 hours sleep from midnight to 0800 hours, sleep is most intense in the early morning at about 0300 hours. There is a mid-afternoon increase in sleep propensity at about 1500 hours that coincides with the mid-afternoon dip in alertness, FIG. 3, and increases in sleep related traffic accidents, FIG. 5.

Figure 10:
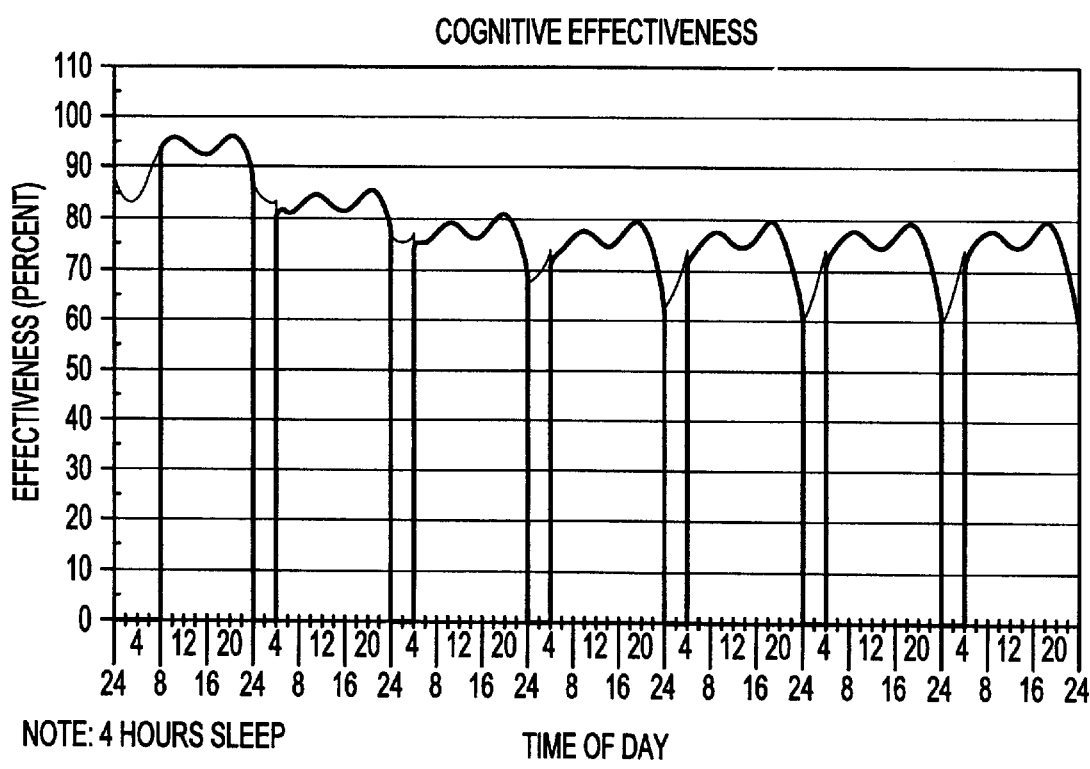
FIG. 10 is a graph illustrating sleep and predictions of cognitive effectiveness with four hours of sleep per night, according to one variation of the present invention (the heavy line is performance while awake)

The method for evaluating effectiveness according to the present invention can be used to predict equilibrium states. A homeostatic representation of sleep regulation leads to an important implication that is seldom recognized. If a subject is scheduled to take less than an optimal amount of sleep each night, for example, four hours per day, the reservoir 70 initially loses more units during the awake period than are made up during the sleep period. This results in a sleep debt at the end of the sleep period that accumulates over days. However, since the rate of sleep accumulation increases with sleep debt, eventually, the rate of sleep accumulation increases such that four hours of sleep makes up for twenty hours awake. At this point, the reservoir 70 reaches an equilibrium state and no further debt is accumulated, although the initial deficit remains as long as the person remains on this schedule. The result of this process is shown in FIG. 10, in which a schedule of one day with 8 hours of sleep followed by six days of 4 hours of sleep per day is illustrated, with each sleep period starting at midnight. By the sixth day of the restricted sleep schedule, cognitive performance oscillates about a stable level well below the baseline level achieved with 8 hours of sleep. Minimum effectiveness is about 60% on the seventh day.

FIG. 10 also illustrates the operation of sleep inertia SI during the first two hours following awakening according to the simulation. With only four hours sleep per night, the average intensity of sleep is high compared to a normal 8 hours sleep period. As a consequence, sleep inertia, which is driven by sleep intensity at time of awakening, is relatively high. This is evident as the initial "notch" in performance immediately after awakening in this seven-day record of performance.

Figure 11:
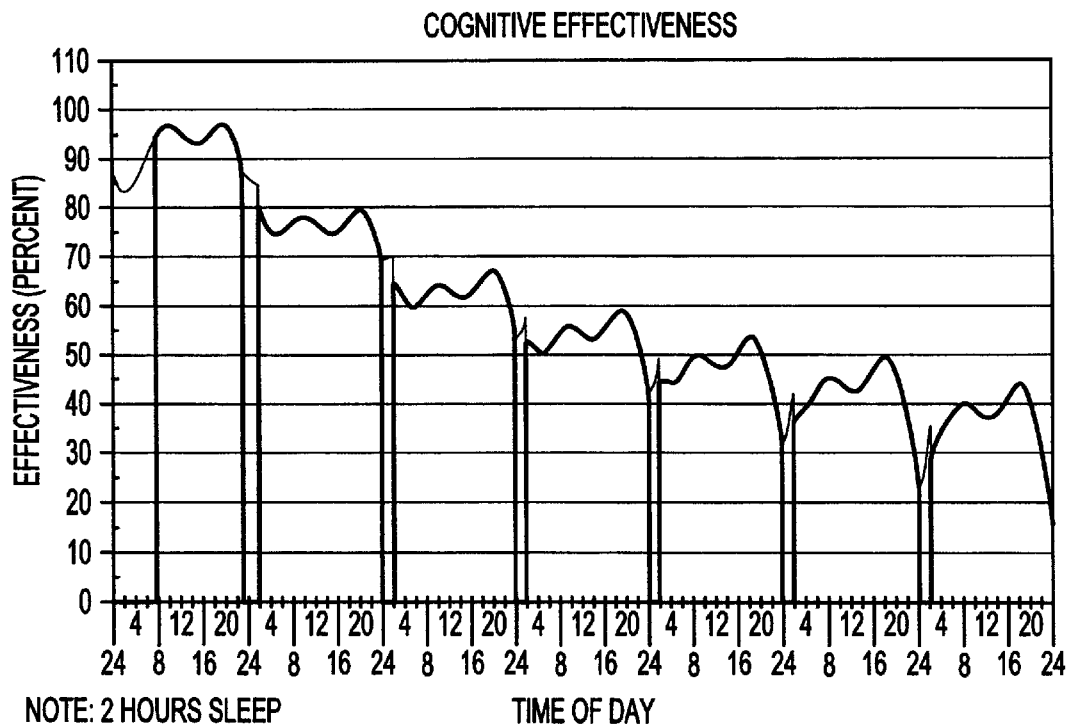
FIG. 11 is a graph illustrating an extended record of sleep and performance under a schedule of only 2 hours of sleep per day, according to one variation of the present invention (the heavy line is performance while awake)

Progressive sleep debt under extreme schedules can also be predicted using the method for evaluating the effectiveness according to the present invention. The sleep homeostat is not infinitely elastic; there is a limit to the rate of sleep accumulation (sleep intensity). Any schedule that provides less than 3 hours of sleep per day (for the average person) will not reach an equilibrium state and performance capacity will gradually deplete to zero, although the rate of depletion slows over the first week of restriction as sleep intensity rises to its maximum level. FIG. 11 is a graph illustrating a simulation of an extended record of sleep and performance under a schedule of only 2 hours of sleep per day. Under such a schedule, minimum performance declines to about 17% at the end of the seventh day.

Figure 12:
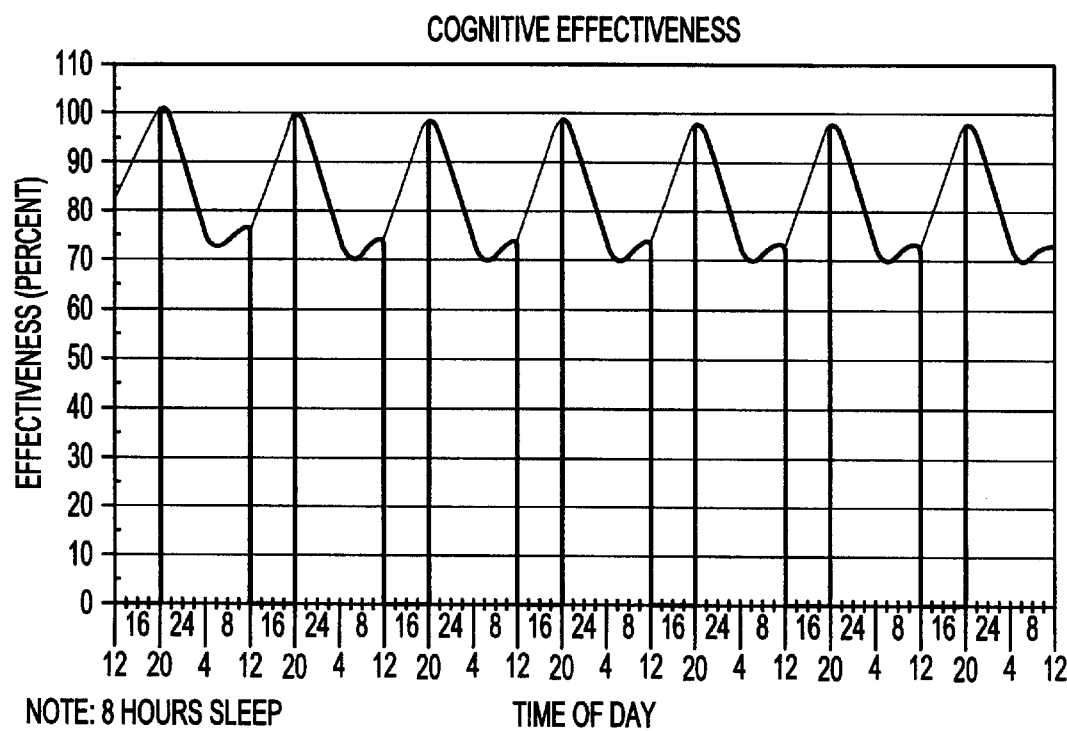
FIG. 12 is a graph illustrating the predicted performance of an individual given eight hours of sleep per day, starting at 1200 hours (noon) each day, according to one variation of the present invention and with phase adjustment deactivated for illustration (the heavy line is performance while awake)

The performance effects of sleep timing can be predicted. The method for evaluating the effectiveness of the present invention is sensitive to the time of day of the sleep period. FIG. 12 illustrates the predicted performance of an individual given eight hours of sleep per day, starting at 1200 hours (noon) each day, 12 hours out of phase from that shown in FIG. 4. Although performance reaches a peak of 100% at the start of each awake period (2000 hours), predicted performance then rapidly declines during the late night and early morning hours to a strong dip at about 0500 hours. Minimum predicted performance under this schedule is predicted to be as low as 69% compared to minimum performance under a normal sleep schedule of 86%. Note that for this chart, the phase correction algorithm was disabled so that the fall effects of out of phase sleep could be visualized.

This alteration in pattern results from two factors. First, sleep intensity is initially less for sleep periods starting at noon. This results in accumulation of a small debt that is quickly offset by the homeostatic sleep mechanism. The second, more persistent pattern is the combined effect of the circadian oscillation of performance that reaches its minimum in the early morning hours and the sixteen hours of accumulated sleep debt at the end of the awake period that predicts a strong dip in effectiveness toward the end of the awake period. This pattern has strong implications for performance under shift schedules that require daytime sleep. It is well documented that most mistakes on the night shift occur during the early morning hours and this outcome is predicted by the present method for evaluating effectiveness.

The system and method for evaluating effectiveness of the present invention can predict changes in cognitive capacity as measured by standard laboratory tests of cognitive performance. It is assumed that these tests measure changes in the fundamental capacity to perform a variety of tasks that rely, more or less, on the cognitive skills of discrimination, reaction time, mental processing, reasoning, and language comprehension and production. However, specific tasks, such as specific military tasks vary in their reliance on these skills, and deficits in cognitive capacity may not produce identical reductions in the capacity to perform all military tasks. It is reasonable to assume, however, that the changes in military task performance would correlate with changes in the underlying cognitive capacity. In other words, if one were to plot changes in military task performance as a function of measured changes in cognitive capacity, there would be a monotonic relationship between the two variables. Therefore, if these two sets of data were available from a test population subjected to sleep deprivation, linear (or non-linear) regression techniques could be applied to derive a transform function; this transform translates predicted cognitive changes into changes in military task performance. Based on this reasoning, the method for evaluating the effectiveness, discussed previously as the cognitive effectiveness 56, can be extended to predict variations in any task or component of a task (given appropriate test data) using the generalized task effectiveness (TE) expression as follows:

$$TE = A(R_t/R_c) + B + C1\,[\cos(2\Pi(T-P)/24) + C2(\cos(4\Pi(T-P-p')/24))] + I,$$

where

A=linear component slope, B=linear component intercept, C1=Circadian weighting factor, C2=12 hr weighting factor, and P=acrophase of the task.

Figure 13A:
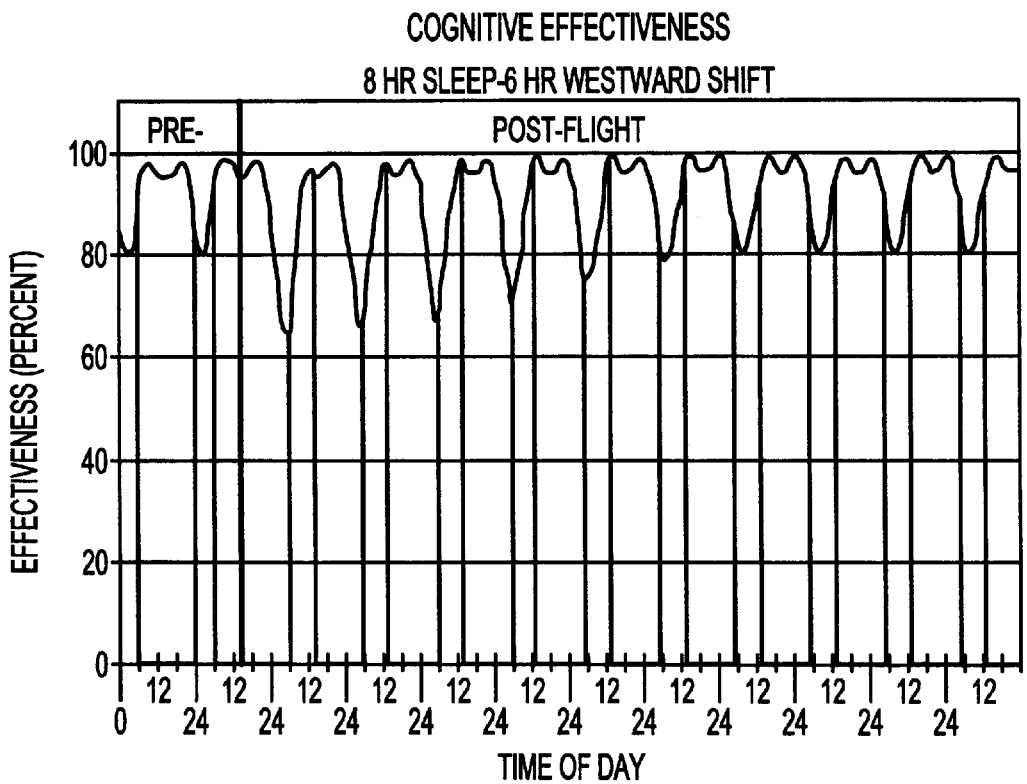
FIG. 13 is a is a graph illustrating the adjustment of performance to two flights, an east-bound flight across six time zones and a west bound flight across 6 time zones, according to one variation of the present invention.
Figure 13B:
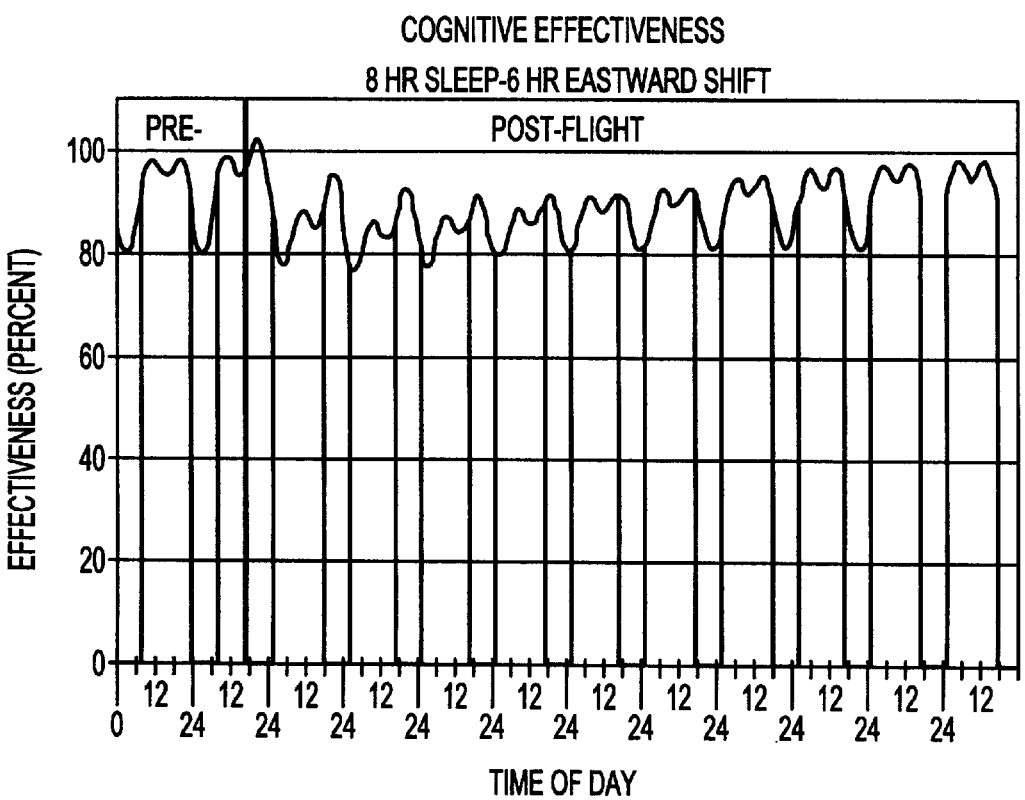

With regard to "Jet Lag" the system and method for evaluating effectiveness can predict the adaptation of performance to changes in time zones that might accompany trans-meridian flights or that might occur if the subject shifts to a regular schedule of nighttime work. FIG. 13 is a graph illustrating the adjustment of performance to two flights, an east-bound flight across six time zones and a west bound flight across 6 time zones.

Predicted performance while awake is more disrupted for a longer period of time by the east bound flight compared to the west bound flight, a commonly reported difference in "jet lag" for east and west plane travel. These effects on performance are a logical and inherent outcome of the interplay of the various processes in the model and do not require a special "jet lag" algorithm. The method for evaluating the effectiveness of the present invention has logic to detect such a change in work pattern and to readjust the phase of the circadian rhythm to the new work pattern indicative of the shift in time zone. The performance prediction was a natural outgrowth of the shifting circadian phase.

When a person moves to another time zone or alters work patterns so that sleep and work occur at different times of day, the internal circadian oscillator that controls body temperature and alertness shifts to this new schedule. During the period of adjustment, a person experiences performance degradation, disrupted mood, and feelings of dysphoria, called circadian desynchronization or "jet lag".

Figure 15:
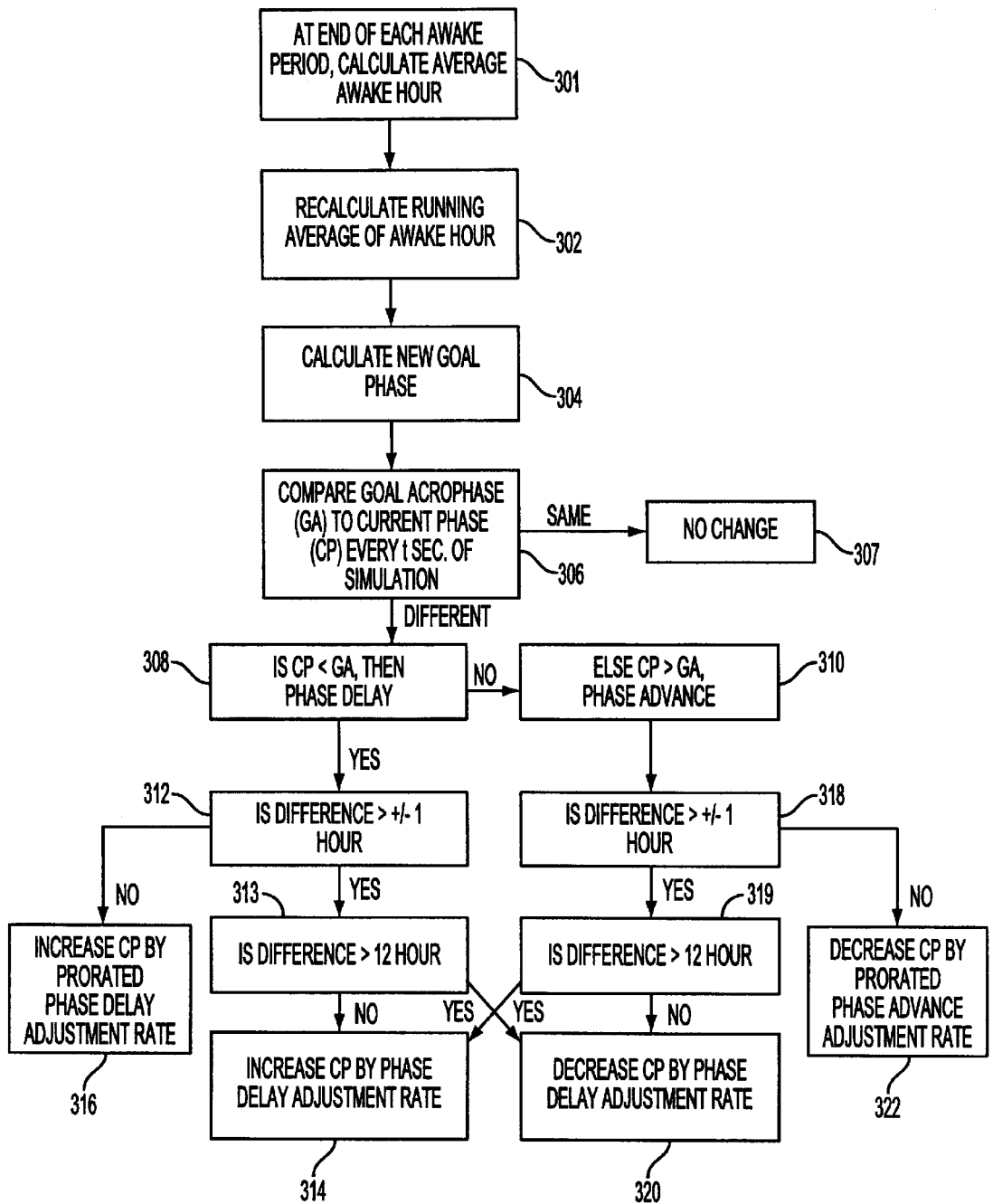
FIG. 15 is a flow chart of a method for adjusting the phase of a person's circadian oscillator based on the timing of major awake periods, according to the present invention.

The method for evaluating the effectiveness of the present invention can simulate this process and automatically adjust the phase of the circadian rhythm to coincide with the activity pattern of the person, at step 212, FIG. 15. Such simulation is important in order to accurately predict the effects of moving to a new time zone or changing to a new and regular work pattern, such as changing from the day shift to the night shift. The method for evaluating the effectiveness detects the average time of the period of wakefulness, and gradually adjusts the time of the peak in the circadian rhythm in relation to the new average awake hour.

The details of the phase adjusting process 212 are charted in FIG. 15. The peak of the circadian rhythm has a reliable relationship to the timing of the period of wakefulness. When a person moves to a new work schedule or a new time zone, the change in average awake time 301 and 302 (relative to a reference time zone) is detected and a new "goal phase" is computed, 304. For example, when moving from the central US time zone to Germany, the awake time of the subject advances six hours. Instead of waking at, say, 0600 Central Time, the subject awakens at 0000 Central Time, which is 0600 German time. This causes a shift of 6 hours in the "goal phase" of the person.

However, the human physiological system does not adapt immediately to such a shift. In general, the speed of adjustment depends on whether the change requires a phase advance or a phase delay. A phase advance (eastward time change) takes about 1.5 days per hour of shift. One embodiment of the present invention adjusts to the new "goal phase" gradually over the course of about nine days for a six hour advance, steps 306, 308, 310, 318, 319, 320, 322. During that time, the performance of the subject will show degradation due to the desynchronization of the internal circadian rhythm from the new rhythm of work and sleep. Likewise, westerly travel causes a phase delay in the circadian rhythm and research shows that phase delays take less time for adjustment, about one day per hour of shift, or six days for a six hour time change, steps 306, 308, 312, 313, 314, 316.

The details of the mathematics of this process are as follows:

A basic premise of the method is that periods of wakefulness provide a strong entrainment stimulus that serves as the basis of phase adjustments to the circadian rhythm. As a result, the time of the period of wakefulness is the primary factor in determining the phase of the circadian rhythm. At the end of each period of wakefulness the model computes a new "running average awake hour," which is the average of that period of wakefulness averaged with the average awake hour of the prior two periods of wakefulness, 301 and 302. Although the wakefulness period is used, this is not to imply that there are not other entrainment stimuli for adjusting the phase of the circadian rhythm such as bright light, activity, etc. Also, brief awakenings during the night lasting only a few minutes (for example, less than 60 minutes) are disregarded.

Based on the running average awake hour, the system computes a new "goal phase" as the running average awake hour plus, for example, 3 hours, 304. For an awake time from 08 to 24 (average of 16), that gives an acrophase of 19, which is a current default.

The system adjusts the current acrophase each minute by comparing the goal to the prior current acrophase. If the difference is greater than 1 hr (+/−1), it starts adjusting the acrophase by $1/1440$ of an hour for each minute of delay (314) or $1/2160$ of an hour for each minute of advance (320). The system adds or subtracts, depending on whether the difference is + or −. If the difference is less than an hour, it adjusts by that difference times $1/1440$ or $1/2160$ each minute, 316 or 322. It checks to see if the difference is greater than 12 hours, in which case it is shorter to go in the opposite direction. In that case, the current acrophase is adjusted by + or −24, and the direction of change is reversed. This method ensures that the current acrophase is adjusted along the shortest path to the goal phase.

The result is a model that adjusts about one hour a day per hour of phase delay and one hour per 1.5 days for each hour of phase advance. It adjusts smoothly and continuously so that it will also deal with rotating shifts, in which case the goal phase shifts back and forth and the adjusting acrophase keeps trying to find the goal at the prescribed rate, but never gets there unless the schedule stabilizes. Other factors, such as bright light or dietary factors may be incorporated as factors that change the rate of adjustment of the physiological rhythm to the predominant schedule represented by the goal phase.

As used herein a number of terms have specific meanings. In particular, the term AVERAGE AWAKE HOUR 301 refers to the average awake hour of any awake period based on the average clock time of the awake period, provided the awake period is one hour or longer. Therefore, a period from 0800 hrs to midnight would have an average clock time of 1600 hrs (the middle of the period). The RUNNING AVERAGE AWAKE HOUR 302 is the average of the average awake hours for the last three periods of wakefulness. The three periods are weighted so that the period just ended has greater weight than either of the two previous periods and the previous period greater weight than the period prior to it, for example $(1x+0.67y+0.33z)/2$.

The term GOAL PHASE is simply the RUNNING AVERAGE AWAKE HOUR plus a constant displacement, which has a default value of +3 hours, 304. This gives a 'standard' acrophase of 1900 hrs for a 16 hour period of wakefulness from 0800 hrs to midnight.

The term ADJUSTING ACROPHASE (steps 306 to 322) refers to a calculation that adjusts at a rate of one hour per day for phase delays or $2/3$ hour per day for phase advance until it is within 1 hour of the goal, and then gradually approaches it from that point to zero deviation. The ADJUSTING ACROPHASE is needed to account for the fact that the biological phase cannot shift in one big jump to the GOAL PHASE.

RUNNING AVERAGE AWAKE HOUR 302

The following is a breakdown of the determination of the RUNNING AVERAGE AWAKE HOUR according to the present invention.

Given:

CA=Cumulative minutes awake at end of awake period.

TAE=Time of awake period end $AH_n$=AVERAGE AWAKE HOUR for awake period n (301).

AV=RUNNING AVERAGE AWAKE minutes (302).

At the end of each awake period calculate new AV, where n=0 is just ended awake period, n=1 is previous awake period, and n=2 is awake period prior to that.

Equation 1a, $AH_n$, AVERAGE AWAKE HOUR for awake period n:

$$AH_n = \text{IF } (TAE-(CA/60)<0), \text{ then } (TAE+24+(TAE+24-(CA/60)))/2),$$

else (TAE+(TAE−(CA/60)))/2)).

Equation 1b, RA, RUNNING AVERAGE AWAKE HOUR:

$$AV = (0.33 \cdot AH_2 + 0.67 \cdot AH_1 + w \cdot AH_0)/(w+1),$$

where $w = CA_0/120$, and minimum value=1.

Explanation:

(TAE−(CA/60)) is the time of the start of the awake period in hours, and (TAE+(TAE−(CA/60)))/2 calculates the AVERAGE AWAKE HOUR 301 as the simple average of the beginning time and ending time. For unusually long awake periods greater than 24 hours, the average hour of the last portion of the awake period less than 24 hrs is averaged with a time 12 hrs after the start of the awake period for each proceeding 24 hour period awake.

AV 302 is calculated as the weighted average of the last three awake periods, such that the just ended period has weight equal to half the duration in hours of the just ended awake period, the two prior periods have a combined weight of one, and the prior period has a weight twice that of the period prior to it.

GOAL PHASE 304

Given: RA=A parameter that sets the RELATIVE ACROPHASE based on the AVERAGE AWAKE HOUR. For example an RA=3 gives an acrophase of 19 by adding it to the AVERAGE AWAKE HOUR of 16 for an awake period from 0800 to 2400. This is a parameter.

GA=GOAL PHASE

Then: at the end of each awake period calculate a new GOAL PHASE:

Equation 2:

$$GA = AV + RA$$

Explanation:

The acrophase of the arousal/temperature rhythm is set relative to the AVERAGE AWAKE HOUR. That is the essence of using the awake time as the entrainment stimulus for the phase shifting model. As average awake hour shifts with a new schedule or time zone, then the goal phase adjusts also. The actual phase of the temperature rhythm does not adjust immediately to this new goal phase, but gradually moves toward it according to the adjustment algorithm discussed next.

ADJUSTING ACROPHASE—PHASE CORRECTION ALGORITHM (306 to 322)

Given: CP=Current Acrophase, $PC_a$=amount of Phase Change in minutes for each hour of advance, default value is 2160 minutes per hour of advance (eastward flight direction), $PC_d$=amount of Phase Change in minutes for each hour of delay, default value is 1440 minutes per hour of delay (westward flight direction).

Then: at each minute of schedule, adjust the current acrophase according to the following algorithm:

Equation 3:

If GA=CP, then no change. 307

If CP<GA: Phase Delay 308

Then, If $GA-CP>1$, 314

If $GA-CP>12$, then New $CP = \text{Old } CP + 24 - 1/PC_a$

Else, New $CP = \text{Old } CP + 1/PC_d$

Else, New $CP = \text{Old } CP + (GA-CP) \cdot 1/PC_d$, 316

If CP>=GA: Phase Advance, 310

Then, $CP - GA > 1$, 320

If $CP-GA>12$, then New $CP = \text{Old } CP - 24 + 1/PC_d$

Else, New $CP = \text{Old } CP - 1/PC_a$

Else, New $CP = \text{Old } CP + (GA-CP) \cdot 1/PC_a$, 322

Explanation:

The initial IF statements 308 and 310 check to see which is greater, GOAL PHASE or CURRENT ACROPHASE. That determines which way to move the CURRENT ACROPHASE, i.e. phase delay or advance.

The next level of IF statements determines if the difference is greater than one hour, the basic unit of change, 312 and 318. If it is greater than one, then the acrophase is moved by +/−1/PC hours; if it is less than one, the acrophase is moved by the difference times 1/PC. This gives an average rate of change of about 1/PC and then approaches the Goal value gradually.

The next level of IF statements determines if the difference is greater than 12 hours, 313 and 319. If it is greater than 12 hours, then 24 is subtracted or added as appropriate and moved in the opposite direction. Otherwise, CP is adjusted by the delay or advance rate as appropriate, 314 or 320. This determines the shortest distance and adjusts the direction of change accordingly.

Note that the method of change when the difference is less than 1 hour is the same expression, regardless of which is greater, GA or CP. This is because the (GA−CP) term will have the appropriate sign to move in the correct direction.

Figure 16:
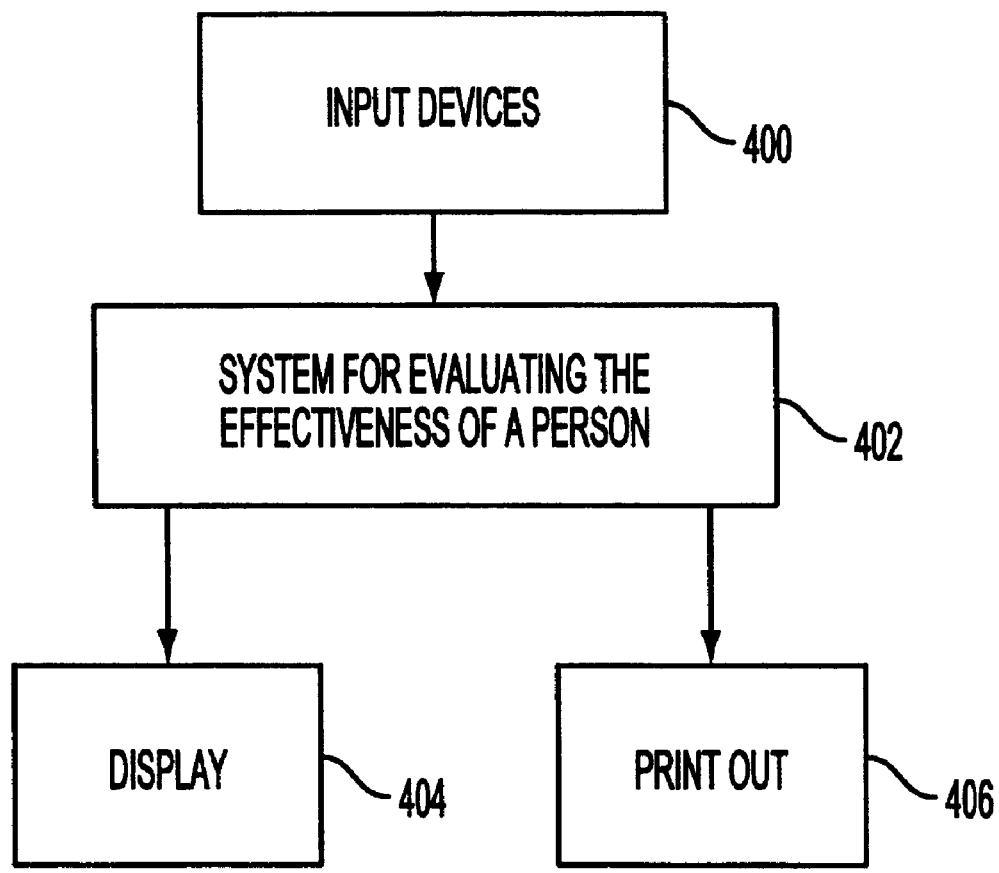
FIG. 16 is a block diagram of a system of evaluating the effectiveness of a person according to the present invention.

FIG. 16 illustrates a block diagram of a system for predicting task effectiveness according to present invention. Data is entered using input devices 400. These input devices 400 may include a keyboard and mouse, a data storage medium from which the data maybe extracted, and sensors that provide time and sleep/wakefulness data.

The system 402 may include a microprocessor that uses the data entered through the input devices 400 to provide results either to the display 404 or the print out 406. These results may be similar to the graphs shown in FIGS. 4, 10, 11, and 12. The system can utilize actual data for a particular person to provide task effectiveness data that is particular to that person, or can be used to predict task effectiveness for the general population or a sub-group of the population.

For example, FIGS. 10 and 11 are graphs illustrating sleep and predictions of cognitive effectiveness with four and two hours of sleep per night, respectively, while FIG. 12 shows a graph of the predicted performance of an individual given eight hours of sleep per day, starting at 1200 hours (noon) each day. These figures illustrate the predictive capacity of the system of the present invention. The raw sleep/wake data is entered, most likely, through a keyboard so that the system can produce the general predictive results, such as shown in FIGS. 10–12.

For a particular person, the actual sleep data may be entered for that person. The data may be entered to the system 402 via a keyboard and/or through sensors that provide the sleep/wake data for that person. Similarly, the data concerning the cognitive skills required for a particular task may be entered using the keyboard or may be downloaded from a storage medium.

Having described several embodiments of the system and method for predicting task effectiveness in accordance with the present invention, it is believed that other modifications, variations and changes will be suggested to those skilled in the art in view of the description set forth above. It is therefore to be understood that all such variations, modifications and changes are believed to fall within the scope of the invention as defined in the appended claims.

What is claimed is:

1. A method of evaluating the effectiveness of a person to perform a task based on previous or predicted sleep pattern comprising the steps of:
   modeling circadian oscillators for the person;
   calculating the amount of effective sleep in a sleep reservoir for the person based on the person's sleep and activity pattern; and
   calculating an effectiveness of the person to perform said task based on said oscillators and said sleep reservoir.

2. A method as recited in claim 1, comprising the further step of calculating a sleep debt.

3. A method as recited in claim 2, further comprising the step of calculating sleep intensity based on said sleep debt.

4. A method as recited in claim 3, wherein said step of modeling circadian oscillators further comprises determining sleep propensity and performance rhythm.

5. A method as recited in claim 4, wherein said step of calculating a sleep intensity is based on sleep propensity and said sleep debt.

6. A method as recited in claim 4, wherein said step of modeling circadian oscillators is done according to the equation:

$$c = \cos(2\Pi(T-p)/24) + \beta\cos(4\Pi(T-p-p')/24),$$

where T=time of day, p=24 hr phase in hours, p'=12 hr relative phase in hrs, and $\beta$=relative amplitude of 12 hour cycle.

7. A method as recited in claim 6, wherein said step of modeling circadian oscillators further comprises determining sleep propensity and performance rhythm, said sleep propensity is determined by the following equation:

$$SP = m - (a_s \cdot c)$$

where m=mesor, and $a_s$=sleep propensity amplitude.

8. A method as recited in claim 7, wherein sleep intensity is determined according to the equation:

$$SI = SP + SD, \text{ in sleep units per minute, } SI \leq SI_{max},$$

where SD is sleep debt.

9. A method as recited in claim 8, comprising the further steps of determining if the person's sleep experienced any fragmentation, and calculating sleep accumulation based on said sleep intensity and said fragmentation, according to the equation:

$$S = SI \cdot t,$$

where t=time interval.

10. A method as recited in claim 6, wherein said step of modeling circadian oscillators further comprises determining sleep propensity and performance rhythm, said performance rhythm is determined by the following equation:

$$C = a_p \cdot c$$

where $a_p = a_1 + a_2(R_c - R_t)/R_c$ performance rhythm amplitude, where $R_c$=Reservoir Capacity, $R_t$=Current Reservoir Balance, $(R_c - R_t)$=Current Reservoir Deficit, $a_1$ is a constant performance rhythm amplitude factor, and $a_2$ is a variable performance rhythm amplitude factor.

11. A method as recited in claim 10, comprising the further steps of determining if the person's sleep experienced any fragmentation and determining sleep inertia for the person, wherein said step of determining sleep inertia is performed according to the equation:

$$I = -1 \cdot I_{max} \cdot e^{-(t_a \cdot 1/SI \cdot i)},$$

where $I_{max}$=maximum reduction of effectiveness during inertia period, and i=inertia time constant for two hours after awakening, wherein said step of calculating said sleep debt is determined by the following equation:

$$SD = f(R_c - R_t),$$

where $R_c$=Reservoir Capacity, $R_t$=Current Reservoir Balance, $(R_c - R_t)$=Current Reservoir Deficit, and f=amplitude of feedback;

wherein said sleep propensity is determined by the following equation:

$$SP = m - (a_s \cdot c),$$

where m=mesor, and $a_s$=sleep propensity amplitude;

wherein said step of determining sleep intensity is performed according to the equation:

$$SI = SP + SD, \text{ in sleep units per minute, } SI \leq SI_{max};$$

wherein sleep accumulation is calculated based on said sleep intensity and fragmentation, according to the equation:

$$S = SI \cdot t,$$

where t=time interval;

said step of calculating the amount of effective sleep in a sleep reservoir is determined by the following function:

$$R_t = R_{t-1} + S - P, \text{ and represents total sleep units at time interval t},$$

where P represents performance use; and said step of calculating the effectiveness is performed using the equation:

$$E = 100(R_t/R_c) + C + I.$$

12. A method as recited in claim 2, wherein said step of calculating said sleep debt is determined by the following equation:

$$SD = f(R_c - R_t),$$

where $R_c$=Reservoir Capacity, $R_t$=Current Reservoir Balance, $(R_c - R_t)$=Current Reservoir Deficit, and f=amplitude of feedback.

13. A method as recited in claim 2, wherein said step of determining the person's sleep debt is based on said amount of effective sleep in the sleep reservoir.

14. A method as recited in claim 1, comprising the further step of determining if the person's sleep experienced any fragmentation.

15. A method as recited in claim 14, comprising the further steps of calculating a sleep debt, calculating sleep intensity based on said sleep debt, and calculating sleep accumulation based on said sleep intensity and said fragmentation.

16. A method as recited in claim 15, wherein said step of calculating the amount of effective sleep in the sleep reservoir is performed based on said sleep accumulation and depletion due to performance use by the person.

17. A method as recited in claim 16, wherein said performance use is calculated according to the equation:

$$P=K \cdot t,$$

where K=performance use rate; and said step of calculating the amount of effective sleep in a sleep reservoir is determined by the following function: $R_t = R_{t-1} + S - P$, and represents total sleep units at time interval t.

18. A method as recited in claim 14, wherein said step of determining if the person's sleep experienced any fragmentation is based on frequency of awakenings from sleep.

19. A method as recited in claim 1, comprising the further step of determining sleep inertia for the person.

20. A method as recited in claim 19, wherein said step of determining sleep inertia is based on sleep intensity at a time of awakening.

21. A method as recited in claim 19, wherein said effectiveness of the person to perform said task is calculated based upon said circadian oscillators, said amount of effective sleep in said sleep reservoir, and said sleep inertia.

22. A method as recited in claim 19, wherein said step of determining sleep inertia is performed according to the equation:

$$I=-1 \cdot I_{max} \cdot e^{-(t_a \cdot 1/SI \cdot i)},$$

where $I_{max}$=maximum reduction of effectiveness during inertia period and i=inertia time constant for two hours after awakening.

23. A method as recited in claim 1, comprising the further step of adjusting phases of said circadian oscillators to reflect new time zones or shift schedules.

24. A method as recited in claim 1, wherein said circadian oscillators are determined by determining a new average awake hour at an end of each period of wakefulness, said new average awake hour being an average of that period of wakefulness averaged with an average awake hour of two prior periods of wakefulness.

25. A method of evaluating the effectiveness of a person to perform a task based on sleep patterns comprising the steps of:

modeling circadian oscillators for the person;

determining the person's sleep debt;

calculating the amount of effective sleep in a sleep reservoir for the person;

determining if the person's sleep experienced any fragmentation; and calculating the effectiveness of the person to perform said task.

26. A method as recited in claim 25, comprising the further step of calculating a sleep intensity to determine a rate of sleep accumulation.

27. A method as recited in claim 26, wherein said step of calculating a sleep intensity is based on sleep propensity and said sleep debt.

28. A method as recited in claim 25, comprising the further step of determining sleep inertia for the person, and wherein said effectiveness of the person to perform said task is calculated based upon said circadian oscillators, said amount of effective sleep in said sleep reservoir, and said sleep inertia.

29. A method as recited in claim 25, wherein said step of modeling circadian oscillators further comprises determining sleep propensity and performance rhythm.

30. A method of evaluating the effectiveness of a person to perform a task based on his/her previous or predicted sleep pattern comprising the steps of:

modeling circadian oscillators for a person including the steps determining sleep propensity and performance rhythm;

calculating a sleep intensity for the person based on said sleep propensity and sleep debt;

determining if the person's sleep experienced any fragmentation;

calculating the amount of effective sleep in a sleep reservoir for the person;

determining the person's sleep debt based on said amount of effective sleep in a sleep reservoir resulting from sleep accumulation;

calculating sleep accumulation based on said sleep intensity and said fragmentation;

determining sleep inertia for the person; and calculating the effectiveness of the person to perform said task based upon said circadian oscillators, said amount of effective sleep in said sleep reservoir, and said sleep inertia.

31. A system of evaluating the effectiveness of a person to perform a task based on sleep pattern comprising:

at least one input device for entering sleep/wake data;

a microprocessor that models circadian oscillators, calculates an amount of effective sleep in a sleep reservoir based on a sleep and activity pattern, and calculates an effectiveness to perform a task based on said oscillators and said sleep reservoir, based on said sleep/wake data; and a display to show said effectiveness results.

32. A system as recited in claim 31, wherein said at least one input device provides data for an individual person.

33. A computer readable medium having computer-executable instructions for evaluating the effectiveness of a person to perform a task based on sleep pattern comprising the steps of:

modeling circadian oscillators for a person;

calculating the amount of effective sleep in a sleep reservoir for the person based on their sleep and activity pattern; and calculating an effectiveness of the person to perform said task based on said oscillators and said sleep reservoir.

34. A computer readable medium having computer-executable instructions for evaluating the effectiveness of a person to perform a task based on sleep pattern, as recited in claim 33, comprising the further step of calculating a sleep debt.

35. A computer readable medium having computer-executable instructions for evaluating the effectiveness of a person to perform a task based on sleep pattern, as recited in claim 34, further comprising the step of calculating sleep intensity based on said sleep debt.

36. A computer readable medium having computer-executable instructions for evaluating the effectiveness of a person to perform a task based on sleep pattern, as recited in claim 34, wherein said step of determining the person's sleep debt is based on said amount of effective sleep in a sleep reservoir.

37. A computer readable medium having computer-executable instructions for evaluating the effectiveness of a person to perform a task based on sleep pattern, as recited in claim 33, comprising the further step of determining if the person's sleep experienced any fragmentation.

38. A computer readable medium having computer-executable instructions for evaluating the effectiveness of a person to perform a task based on sleep pattern, as recited in claim 37, comprising the further steps of calculating a sleep debt, calculating sleep intensity based on said sleep debt, and calculating sleep accumulation based on said sleep intensity and said fragmentation.

39. A computer readable medium having computer-executable instructions for evaluating the effectiveness of a person to perform a task based on sleep pattern, as recited in claim 38, wherein said step of calculating the amount of effective sleep in a sleep reservoir is performed based on said sleep accumulation and depletion due to performance use by said person.

40. A computer readable medium having computer-executable instructions for evaluating the effectiveness of a person to perform a task based on sleep pattern, as recited in claim 35, comprising the further step of determining sleep inertia for the person.

41. A computer readable medium having computer-executable instructions for evaluating the effectiveness of a person to perform a task based on sleep pattern, as recited in claim 40, wherein said step of determining sleep inertia is based on the sleep intensity at a time of awakening.

42. A computer readable medium having computer-executable instructions for evaluating the effectiveness of a person to perform a task based on sleep pattern, as recited in claim 33, wherein said step of modeling circadian oscillators further comprises determining sleep propensity and performance rhythm.

43. A computer-readable medium having computer-executable instructions for evaluating the effectiveness of a person to perform a task based on sleep pattern comprising the steps of:
　　modeling circadian oscillators for a person including the steps of modeling circadian oscillators further comprises determining sleep propensity and performance rhythm;
　　calculating a sleep intensity for the person based on said sleep propensity and said sleep debt;
　　determining if the person's sleep experienced any fragmentation;
　　calculating the amount of effective sleep in a sleep reservoir for the person;
　　determining the person's sleep debt based on said amount of effective sleep in a sleep reservoir resulting from sleep accumulation;
　　calculating sleep accumulation based on said sleep intensity and said fragmentation;
　　determining sleep inertia for the person; and
　　calculating the effectiveness of the person to perform said task based upon said circadian oscillators, said amount of effective sleep in said sleep reservoir, and said sleep inertia.

44. A computer-readable medium having computer-executable instructions for evaluating the effectiveness of a person to perform a task based on sleep pattern, as recited in claim 43, wherein said method is homeostatic, so that gradual decreases in sleep debt decrease said sleep intensity, and progressive increases in said sleep debt produce an increase in said sleep intensity.

45. A computer-readable medium having computer-executable instructions for evaluating the effectiveness of a person to perform a task based on sleep pattern comprising the steps of:
　　modeling circadian oscillators for the person;
　　determining the person's sleep debt;
　　calculating the amount of effective sleep in a sleep reservoir for the person;
　　determining if the person's sleep experienced any fragmentation; and
　　calculating the effectiveness of the person to perform said task.

46. A computer-readable medium having computer-executable instructions for evaluating the effectiveness of a person to perform a task based on sleep pattern, as recited in claim 45, comprising the further step of calculating a sleep intensity.

47. A computer-readable medium having computer-executable instructions for evaluating the effectiveness of a person to perform a task based on sleep pattern, as recited in claim 45, comprising the further step of determining sleep inertia for the person.

48. A computer-readable medium having computer-executable instructions for evaluating the effectiveness of a person to perform a task based on sleep pattern, as recited in claim 45, wherein said step of modeling circadian oscelators further comprises determining sleep propensity and performance rhythm.

\* \* \* \* \*

UNITED STATES PATENT AND TRADEMARK OFFICE
CERTIFICATE OF CORRECTION

PATENT NO. : 6,579,233 B2
DATED : June 17, 2003
INVENTOR(S) : Steven Rawlings Hursh It is certified that error appears in the above-identified patent and that said Letters Patent is hereby corrected as shown below:

Column 15,
Lines 47-49, "$SI \leqq SI_{Max}$" has been replaced with -- $SI \leq SI_{Max}$ --.

Column 16,
Lines 32-34, "$SI \leqq SI_{Max}$" has been replaced with -- $SI \leq SI_{Max}$ --.

Column 20,
Line 46, "oscelators" has been replaced with -- oscillators --.

Signed and Sealed this

Twenty-eighth Day of October, 2003

JAMES E. ROGAN
*Director of the United States Patent and Trademark Office*